United States Patent

McCaul et al.

[11] Patent Number: 6,150,661
[45] Date of Patent: Nov. 21, 2000

[54] GAS SPECTROSCOPY

[75] Inventors: Bruce W. McCaul, 1370 Lincoln Ave., Palo Alto, Calif. 94301; David E. Doggett, Sunnyvale, Calif.

[73] Assignee: Bruce W. McCaul, Palo Alto, Calif.

[21] Appl. No.: 08/363,094

[22] Filed: Dec. 21, 1994

Related U.S. Application Data

[62] Division of application No. 08/049,474, Apr. 16, 1993, Pat. No. 5,448,071.

[51] Int. Cl.[7] .................................................. G01N 21/17
[52] U.S. Cl. ........................................ 250/343; 250/341.3
[58] Field of Search ............................... 250/343, 341.1, 250/341.3; 372/98, 103

[56] References Cited

U.S. PATENT DOCUMENTS

| | | |
|---|---|---|
| 3,683,410 | 8/1972 | Fowler . |
| 3,683,700 | 8/1972 | Wilfong . |
| 3,699,471 | 10/1972 | Mulready et al. ........................ 372/98 |
| 3,723,731 | 3/1973 | Blau, Jr. . |
| 3,726,270 | 4/1973 | Griffis et al. . |
| 3,726,271 | 4/1973 | Mondshine et al. . |
| 3,829,694 | 8/1974 | Goto . |
| 3,831,589 | 8/1974 | Deering et al. . |
| 3,906,513 | 9/1975 | Siegelman et al. . |
| 3,995,960 | 12/1976 | Fletcher et al. . |
| 4,068,125 | 1/1978 | Bell . |
| 4,084,906 | 4/1978 | Bibbero . |
| 4,085,741 | 4/1978 | Rotgans . |
| 4,361,802 | 11/1982 | Luijpers . |
| 4,368,740 | 1/1983 | Binder . |
| 4,370,152 | 1/1983 | Luper . |
| 4,410,273 | 10/1983 | Mantz et al. . |
| 4,418,701 | 12/1983 | Luijpers . |
| 4,440,177 | 4/1984 | Anderson et al. . |
| 4,448,058 | 5/1984 | Jaffe et al. . |
| 4,463,764 | 8/1984 | Anderson et al. . |
| 4,489,239 | 12/1984 | Grant et al. . |
| 4,492,862 | 1/1985 | Grynberg et al. . |
| 4,498,737 | 2/1985 | Doggert . |
| 4,509,551 | 4/1985 | Luper . |
| 4,537,058 | 8/1985 | Luper . |
| 4,546,793 | 10/1985 | Stupecky . |
| 4,557,603 | 12/1985 | Oehler et al. . |
| 4,581,714 | 4/1986 | Reid . |
| 4,586,149 | 4/1986 | Stillman et al. . |
| 4,601,293 | 7/1986 | Foster et al. . |
| 4,608,344 | 8/1986 | Carter et al. . |
| 4,637,987 | 1/1987 | Minten et al. . |
| 4,638,661 | 1/1987 | Bergmans . |
| 4,668,257 | 5/1987 | van der Meer et al. . |
| 4,677,078 | 6/1987 | Minten et al. . |
| 4,684,258 | 8/1987 | Webster . |
| 4,684,805 | 8/1987 | Shu-Ti Lee et al. . |

(List continued on next page.)

FOREIGN PATENT DOCUMENTS

| | | |
|---|---|---|
| 0176329 | 4/1986 | European Pat. Off. ................. 372/98 |
| 26 35 171 A1 | 2/1978 | Germany . |
| 41 22 572 A1 | 1/1993 | Germany . |
| 2 165 640 | 4/1986 | United Kingdom . |
| 87 07018 | 11/1987 | WIPO . |
| WO 90/00732 | 1/1990 | WIPO . |

OTHER PUBLICATIONS

Hill, D.W. et al., "Cross–Sensitivity Effects in Non–Dispersive Infra–Red Gas Analysers Using Condenser Microphone Detectors", J. Sci. Instrum. (1967), pp. 189–194, vol. 44.

(List continued on next page.)

*Primary Examiner*—Edward P. Westin
*Assistant Examiner*—Richard Hanig
*Attorney, Agent, or Firm*—Skjerven, Morrill, MacPherson, Franklin & Friel LLP; Alan H. MacPherson

[57] ABSTRACT

An absorption spectroscopy device for determining the concentration of a gas (such as oxygen) in a sample cell includes a neutral density absorber or a quarter wave plate. Laser radiation from a laser diode passes through the neutral density absorber or the quarter wave plate, then passes through the sample cell, and then is incident upon a detector. In some embodiments, the laser diode is driven with a drive current having a stepped periodic waveform.

12 Claims, 39 Drawing Sheets

U.S. PATENT DOCUMENTS

| | | |
|---|---|---|
| 4,697,450 | 10/1987 | Bachman et al. . |
| 4,705,617 | 11/1987 | Beebe et al. . |
| 4,719,910 | 1/1988 | Jensen . |
| 4,730,112 | 3/1988 | Wong . |
| 4,747,402 | 5/1988 | Reese et al. . |
| 4,748,632 | 5/1988 | Preston . |
| 4,780,613 | 10/1988 | Berstein et al. . |
| 4,796,639 | 1/1989 | Snow et al. . |
| 4,800,886 | 1/1989 | Nestor . |
| 4,805,122 | 2/1989 | McDavid et al. . |
| 4,805,612 | 2/1989 | Jensen . |
| 4,821,709 | 4/1989 | Jensen . |
| 4,824,242 | 4/1989 | Frick et al. . |
| 4,849,637 | 7/1989 | Cerff et al. . |
| 4,867,571 | 9/1989 | Frick et al. . |
| 4,883,963 | 11/1989 | Kemeny et al. . |
| 4,886,358 | 12/1989 | Pellenbarg et al. . |
| 4,898,465 | 2/1990 | Crawford et al. . |
| 4,901,325 | 2/1990 | Kato et al. . |
| 4,924,095 | 5/1990 | Swanson, Jr. . |
| 4,930,519 | 6/1990 | Anderson et al. . |
| 4,934,816 | 6/1990 | Silver et al. . |
| 4,937,448 | 6/1990 | Mantz et al. . |
| 4,963,004 | 10/1990 | Sato et al. ................................ 372/98 |
| 4,968,887 | 11/1990 | Wong . |
| 4,969,702 | 11/1990 | Anderson . |
| 4,995,256 | 2/1991 | Norlien et al. . |
| 5,012,101 | 4/1991 | Goodall et al. ......................... 250/343 |
| 5,026,991 | 6/1991 | Goldstein et al. ...................... 250/343 |
| 5,032,435 | 7/1991 | Biefeld et al. . |
| 5,038,773 | 8/1991 | Norlien et al. . |
| 5,042,500 | 8/1991 | Norlien et al. . |
| 5,047,639 | 9/1991 | Wong . |
| 5,061,857 | 10/1991 | Thompson et al. . |
| 5,093,837 | 3/1992 | Edwards .................................... 372/98 |
| 5,094,819 | 3/1992 | Yager et al. . |
| 5,096,671 | 3/1992 | Kane et al. . |
| 5,119,825 | 6/1992 | Huhn . |
| 5,124,130 | 6/1992 | Costello et al. . |
| 5,129,401 | 7/1992 | Corenman et al. ..................... 128/716 |
| 5,146,294 | 9/1992 | Grisar et al. . |
| 5,173,749 | 12/1992 | Tell et al. . |
| 5,267,019 | 11/1993 | Whittaker et al. . |
| 5,297,558 | 3/1994 | Acorn et al. . |
| 5,303,712 | 4/1994 | Van Duren . |
| 5,305,762 | 4/1994 | Acorn et al. . |
| 5,307,794 | 5/1994 | Rauterkus et al. . |
| 5,343,818 | 9/1994 | McCarthy et al. . |

OTHER PUBLICATIONS

Nippon Electric Glass America, Inc. data sheet for "Lenslet" Lens for Optical Module, Ref. No. 9310–26E, Jul. 1994, 2 pages.

Philip C. Hobbs, "Research Report: Shot Noise Limited Optical Measurements at Baseband With Noisy Lasers", IBM Research Division, Engineering Technology RC 16199 (#71972) Oct. 17, 1990, 27 pgs.

R.J. Smith et al., "Dart: A Novel Sensor For Helicopter Flight Safety", Photonics Spectra, Jul. 1992, pp. 110–116.

Combitech Group Saab Missiles, Saab Diodair 2000 Data Sheet, "Laser Sensor System for On–line Gas Monitoring", 4 pgs.

Combitech Group Saab Missiles, Saab Diodair 2000 Data Sheet, "Laser Sensor System for In–situ measurement of oxygen", 1 pg.

Combitech Group Saab Missiles, Saab Diodair 2000 Data Sheet, "Laser Sensor System for In–situ measurement of ammonia", 1 pg.

Joel A. Silver, "Frequency–modulation spectroscopy for trace species detection: theory and comparison among experimental methods", Applied Optics, vol. 31, No. 6, Feb. 20, 1992, pp. 707–717.

David S. Bomse et al., "Frequency modulation and wavelength modulation spectroscopies: comparison of experimental methods using a lead–salt diode laser", Applied Optics, vol. 31, No. 6, Feb. 20, 1992, pp. 718–731.

Daniel T. Cassidy, "Trace gas detection using 1.3 $\mu$m InGaAsP diode laser transmitter modules", Applied Optics, vol. 27, No. 3, Feb. 1, 1988, pp. 610–614.

Svante Höjer, et al., "Measurements of electric field strength in gas insulated high–voltage components using infrared diode laser absorption spectroscopy", Applied Optics, vol. 25, No. 17, Sep. 1, 1986, pp. 2984–2987.

H. Ahlberg et al., "IR–Laser Spectroscopy For Measurement Applications In The Industrial Environment", Institute of Electrical Measurements TR 85170, Chalmers University of Technology, Göteborg, Sweden, Dec. 1985, 8 pgs.

S. Lundqvist, et al., "Measurements of pressure–broadening coefficients of NO and $0_3$ using a computerized tunable diode laser spectroscopy", Applied Optics vol. 21, No. 17, Sep. 1, 1982, pp. 3109–3113.

R.S. Eng, et al., "Tunable diode laser spectroscopy: an invited review", Optical Engineering, vol. 19, No. 6, Nov./Dec. 1980, pp. 945–960.

M. Bobb, "Diode–Laser Collimators Suit Communication Applications In Space", Laser Focus/Electro–Optics, p. 79.

"Characteristics of Laser Diodes", Optics Guide V—Melles Griot Supply Catalog, 1990, pp. 9–35.

Optima Precision, Inc. Price List, Jun. 1991 1 pg.

Schematic Diagram of Aspheric Plastic Lens, Optima Precision, Inc., Jan./Feb. 1990, 3 pgs.

Optima Precision, Inc., Specification sheet, Jul. 1987, 1 pg.

"Laser Diode Collimators", D.O. Industries Specification sheet, pp. 2–8.

Siemens Optoelectronics Data Book, 1990, 2 pgs.

Diverse Optics, Inc., Specification sheet, 3 pgs.

Mitsubishi Optoelectronics Data Book, Mitsubishi Electric, 1990, pp. 31–2 to 3–15.

J. Snyder, et al., "Cylindrical microlenses improve laser-–diode beams", Laser Focus World, Feb. 1993, pp. 97–99.

J. Snyder, et al., "Fast, inexpensive, diffraction limited cylindrical microlenses", SPIE Proceedings Reprint vol. 1544, Miniature and Micro–Optics Fabrication and System Applications, 1991, pp. 146–151.

Blue Sky Research Data sheeet, "New High–Efficiency Fiber Coupling Concepts" 1993, 3 pages.

Blue Sky Research Data sheet, "Virtual Point Source Optics For Laser Diodes" Sep. 1992, 1 pg.

Blue Sky Research Price Sheet, 1992, 1 pg.

Blue Sky Research Data sheet, "SAC Series $\mu$lens Single Axis Collimator", Mar. 1993, 1 pg.

J. Snyder, et al., "Fast diffraction–limited cylindrical microlenses", Applied Optics, vol. 30, No. 19, Jul. 1, 1991, pp. 2743–2747.

Optima Precision, Inc. Data sheet, "Laser Diode Collimating and Objective Lens", May 1991, 2 pgs.

Optima Precision, Inc. Data sheet, "Collimated Diode Lasers and Mounting Kit", May 1991, 2 pgs.

Willard et al., 1982, Instrumental Methods of Analysis, 6th ed., p. 82.

OXYGEN < 25%

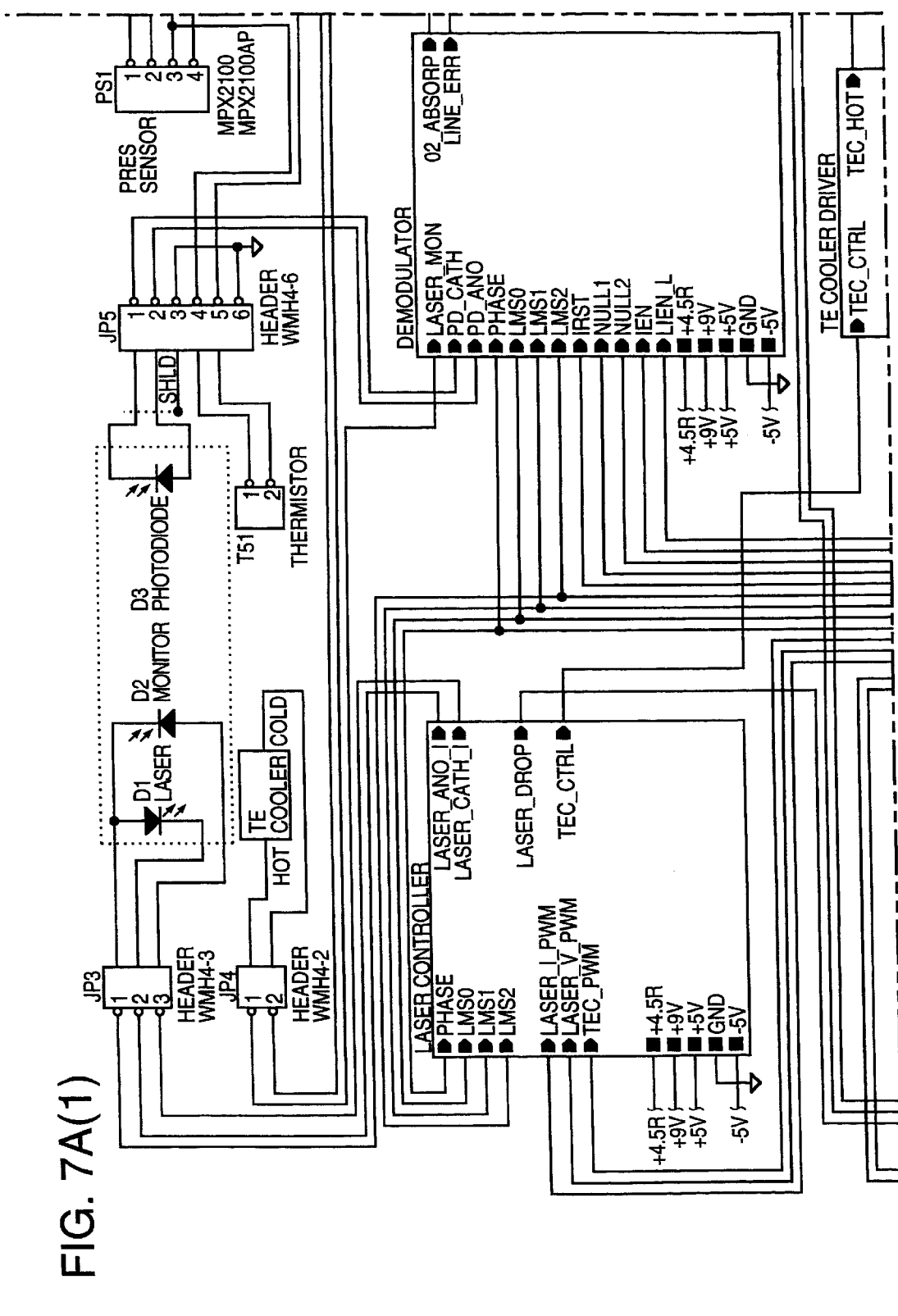
FIG. 7A(1)

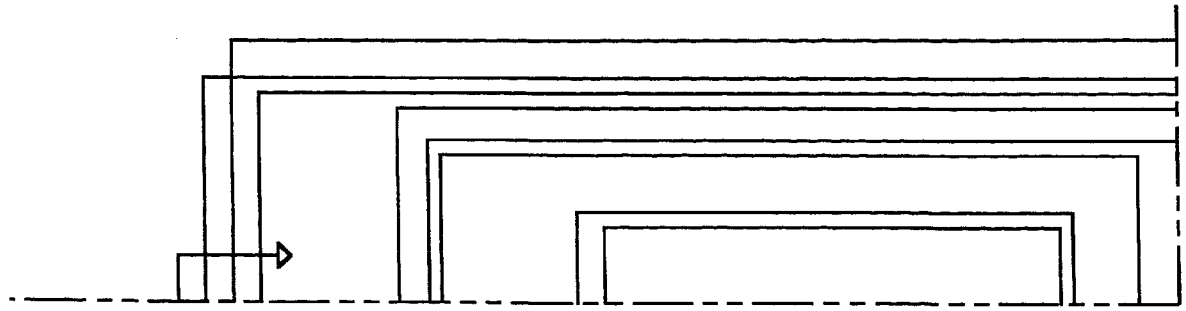
FIG. 7A(2)

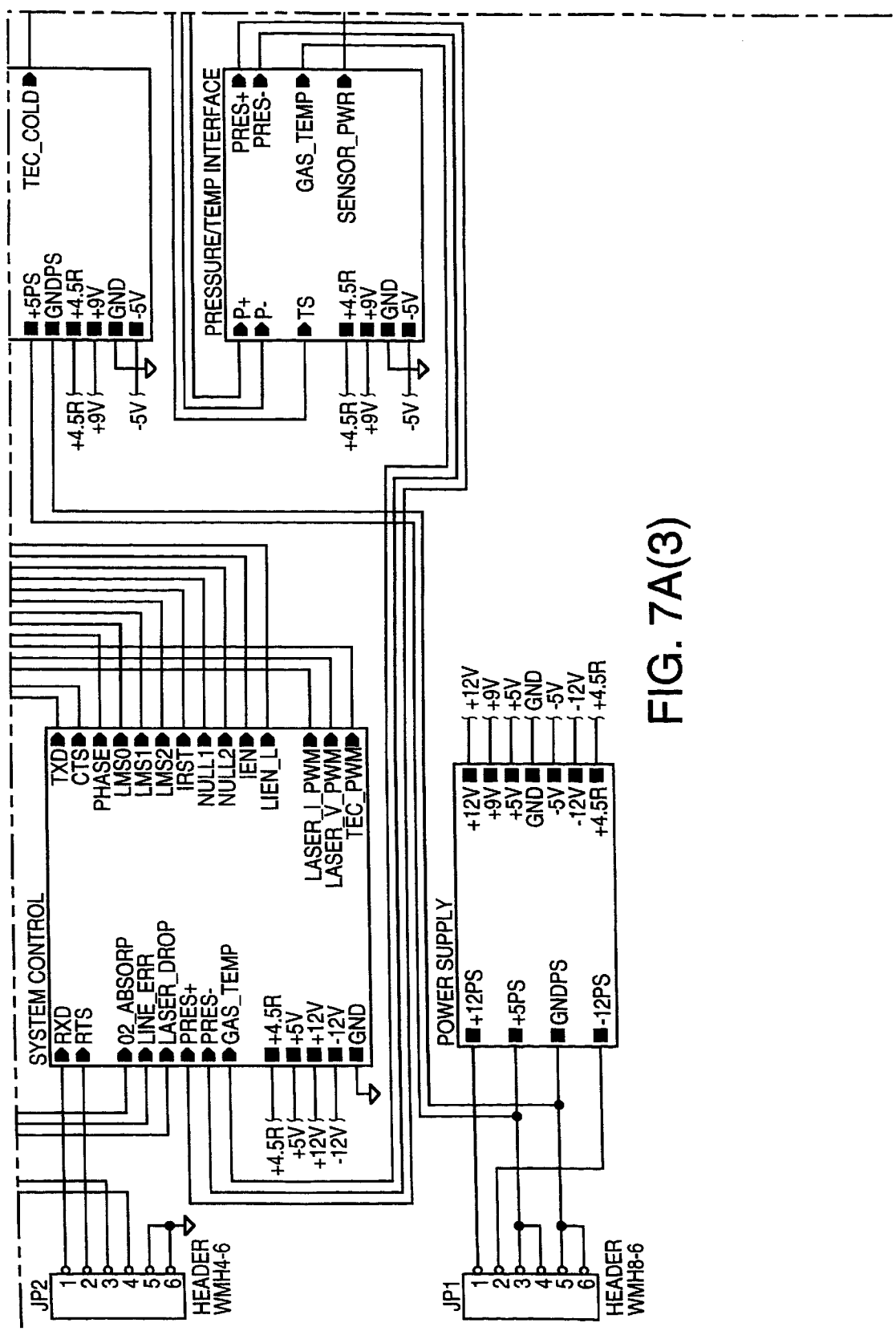
FIG. 7A(3)

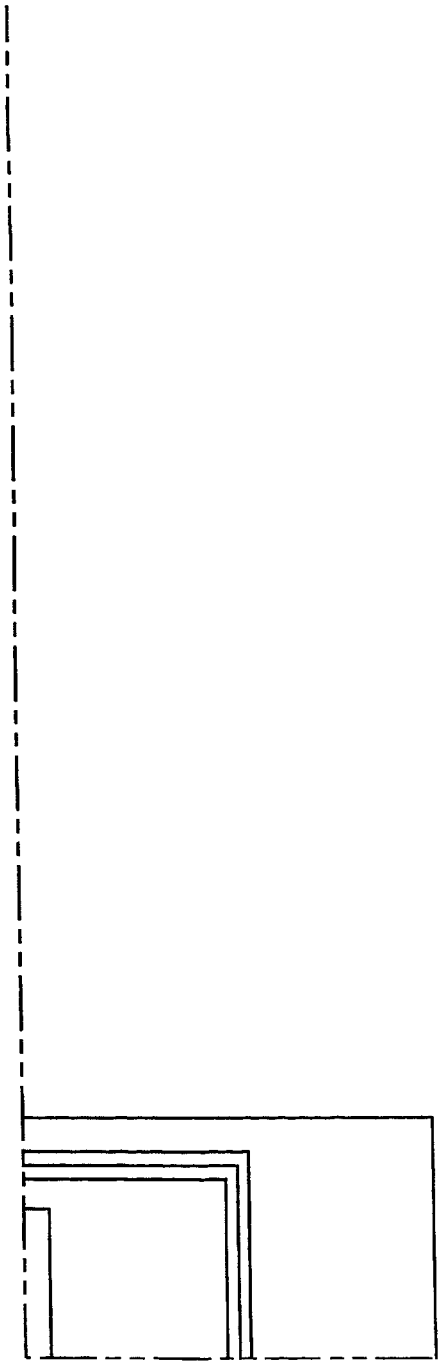

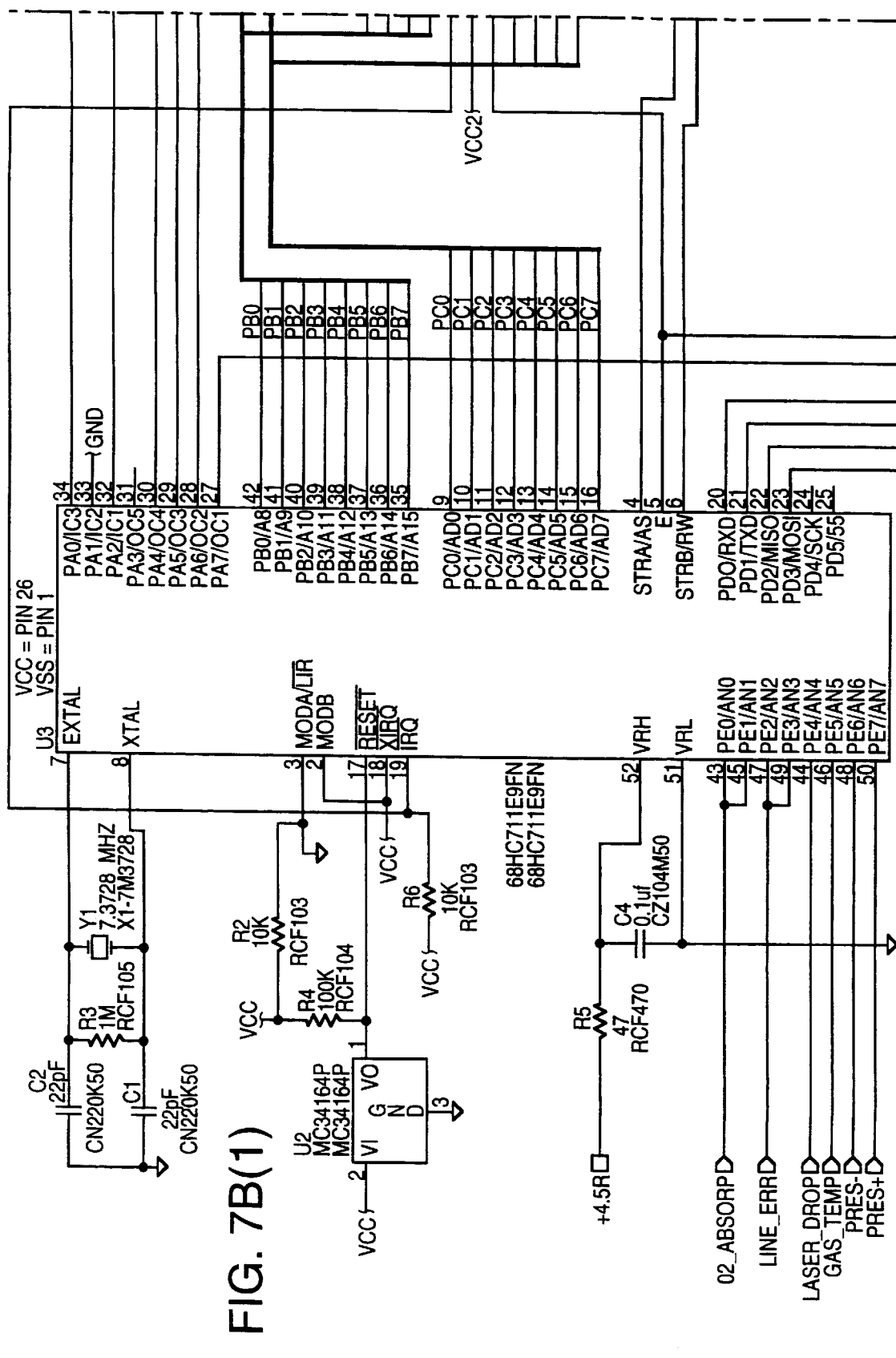
FIG. 7B(1)

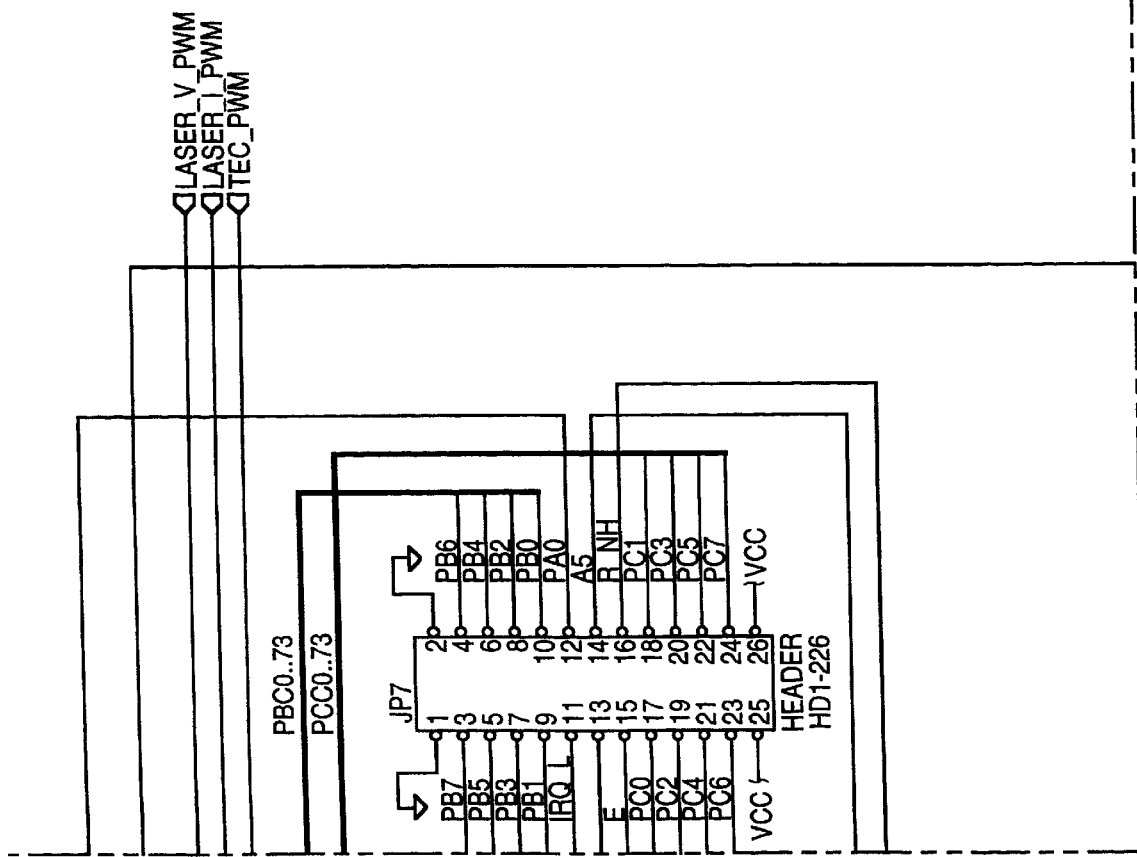
FIG. 7B(2)

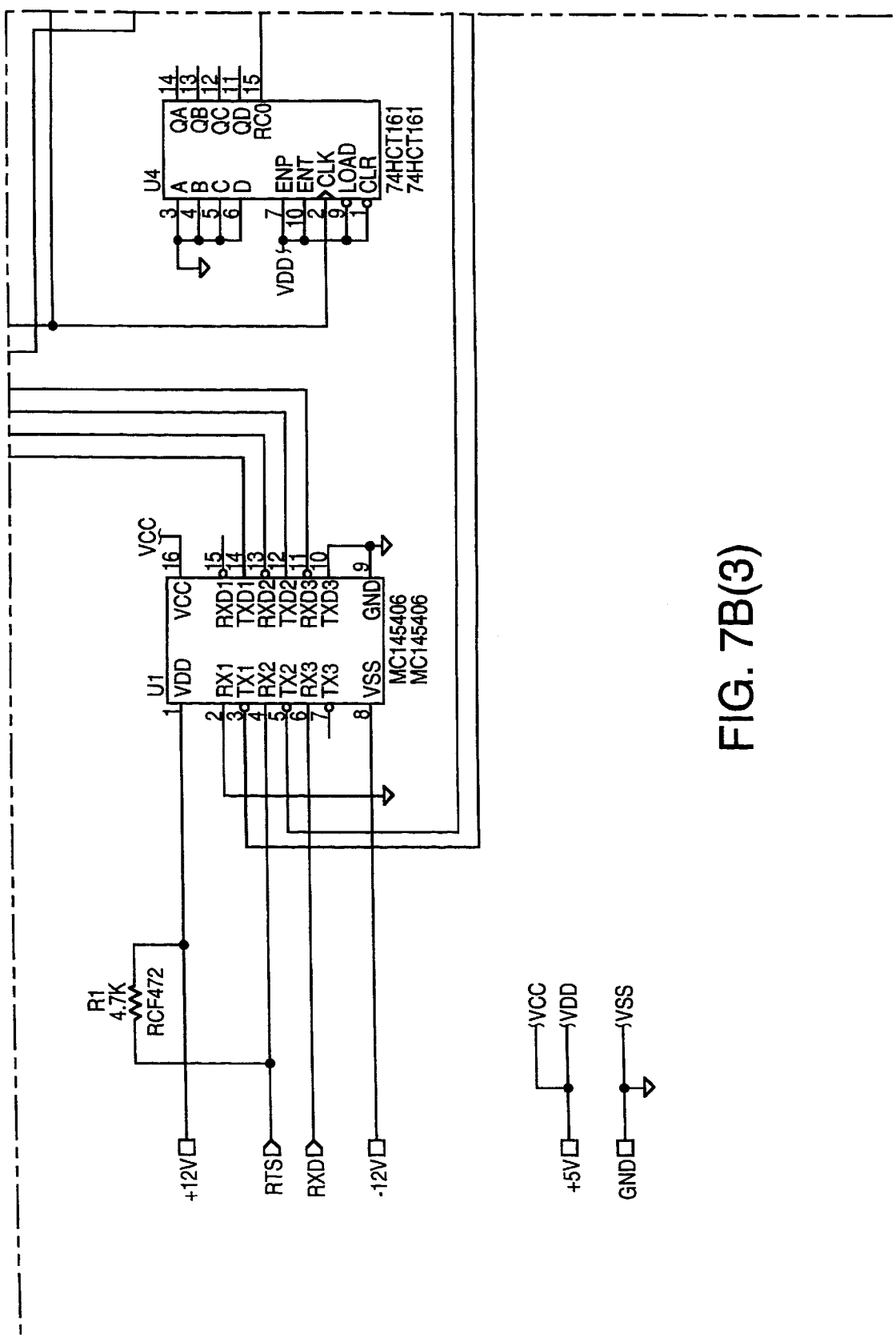
FIG. 7B(3)

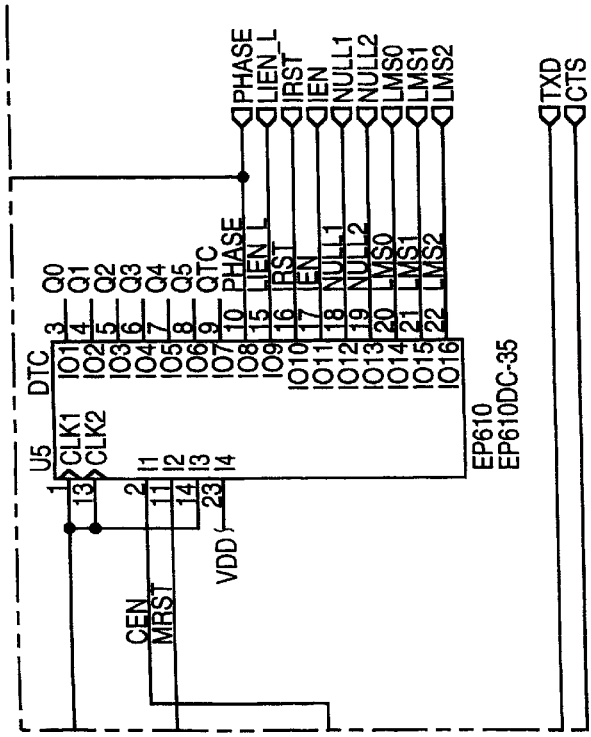

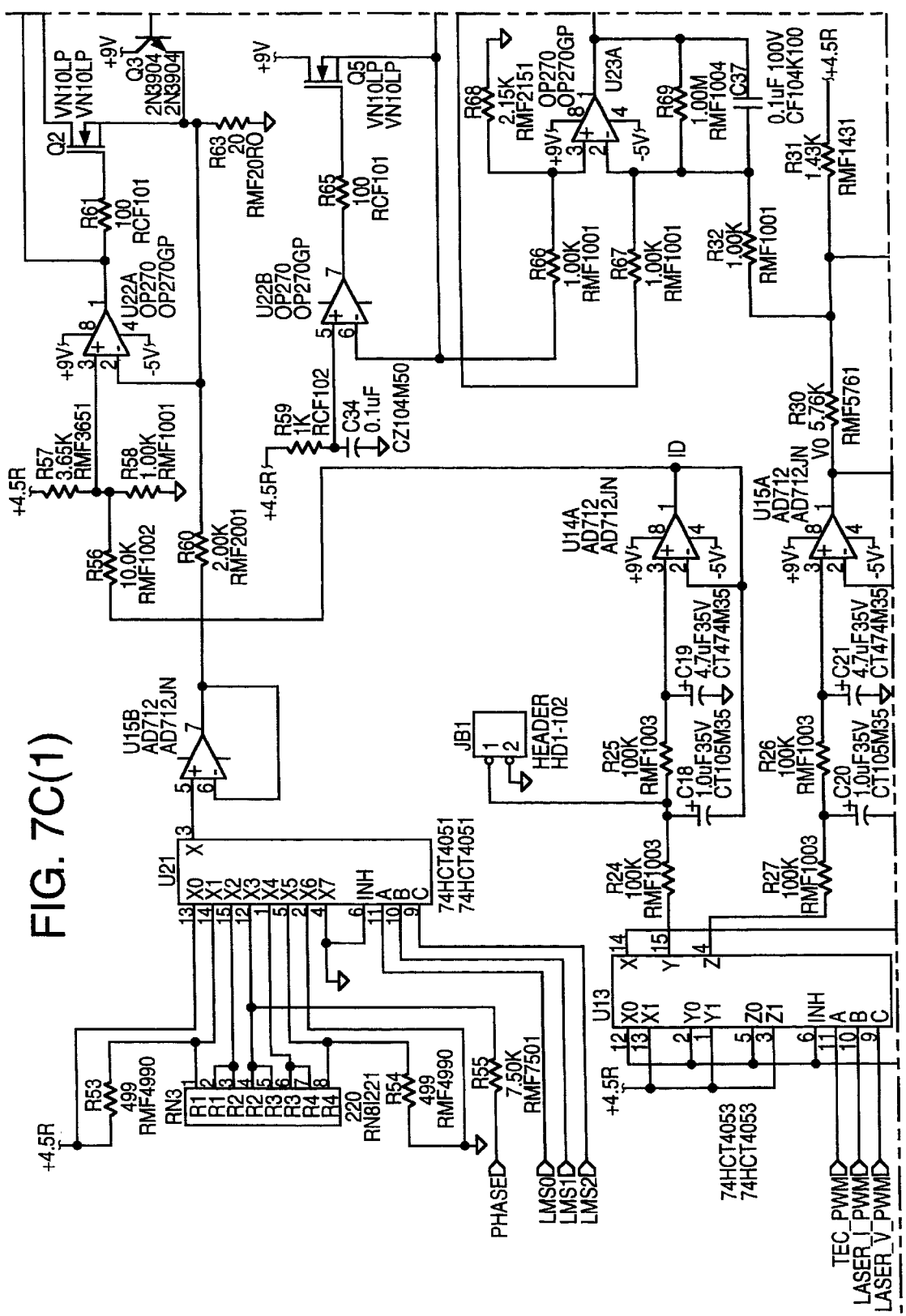
FIG. 7C(1)

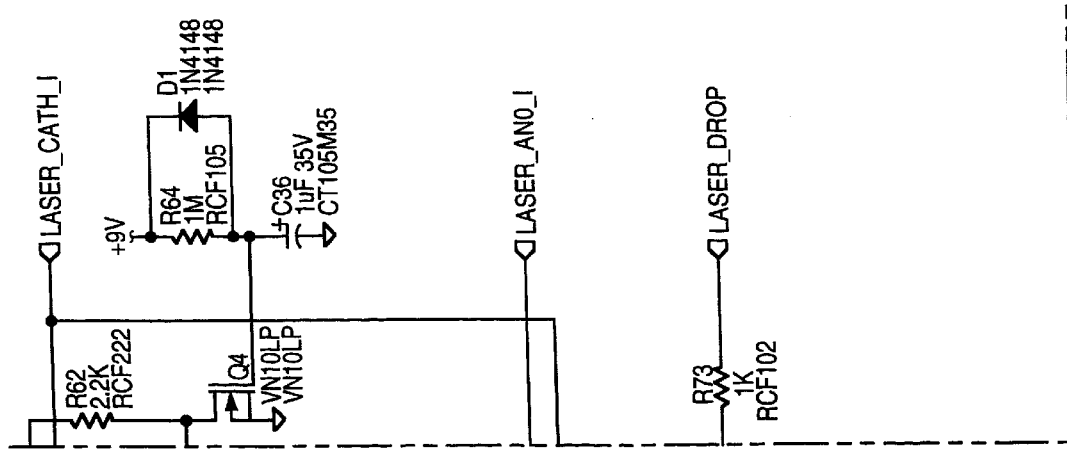
FIG. 7C(2)

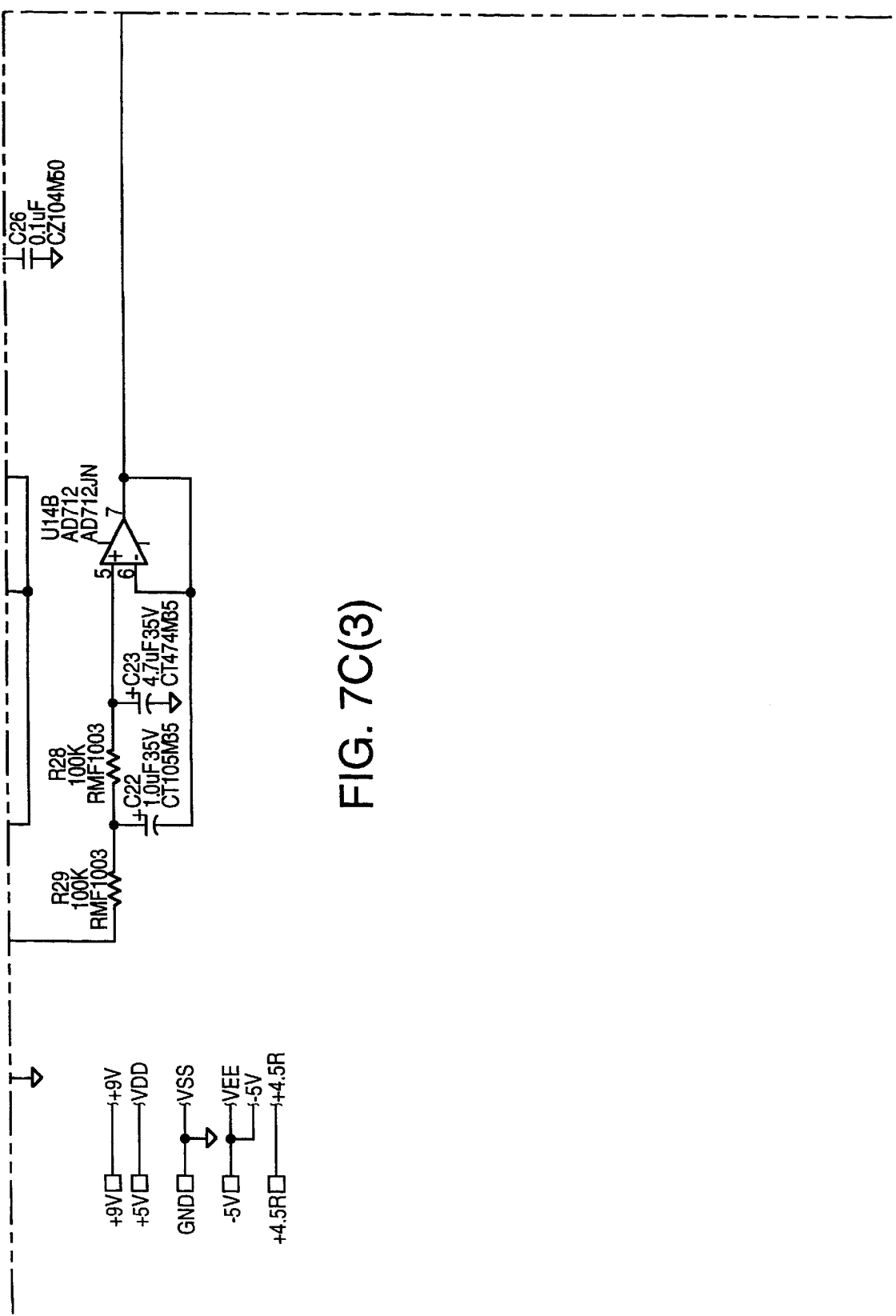
FIG. 7C(3)

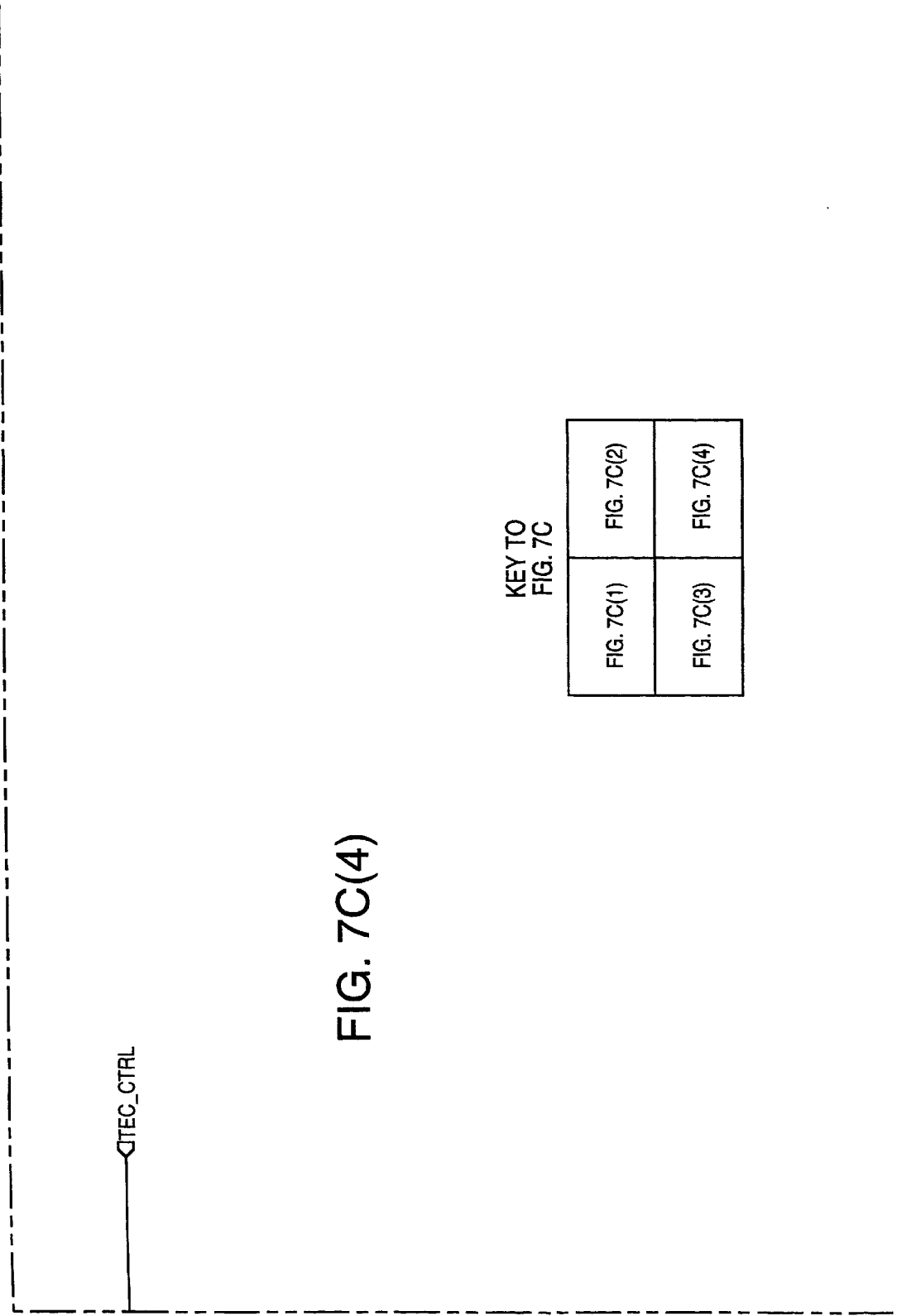

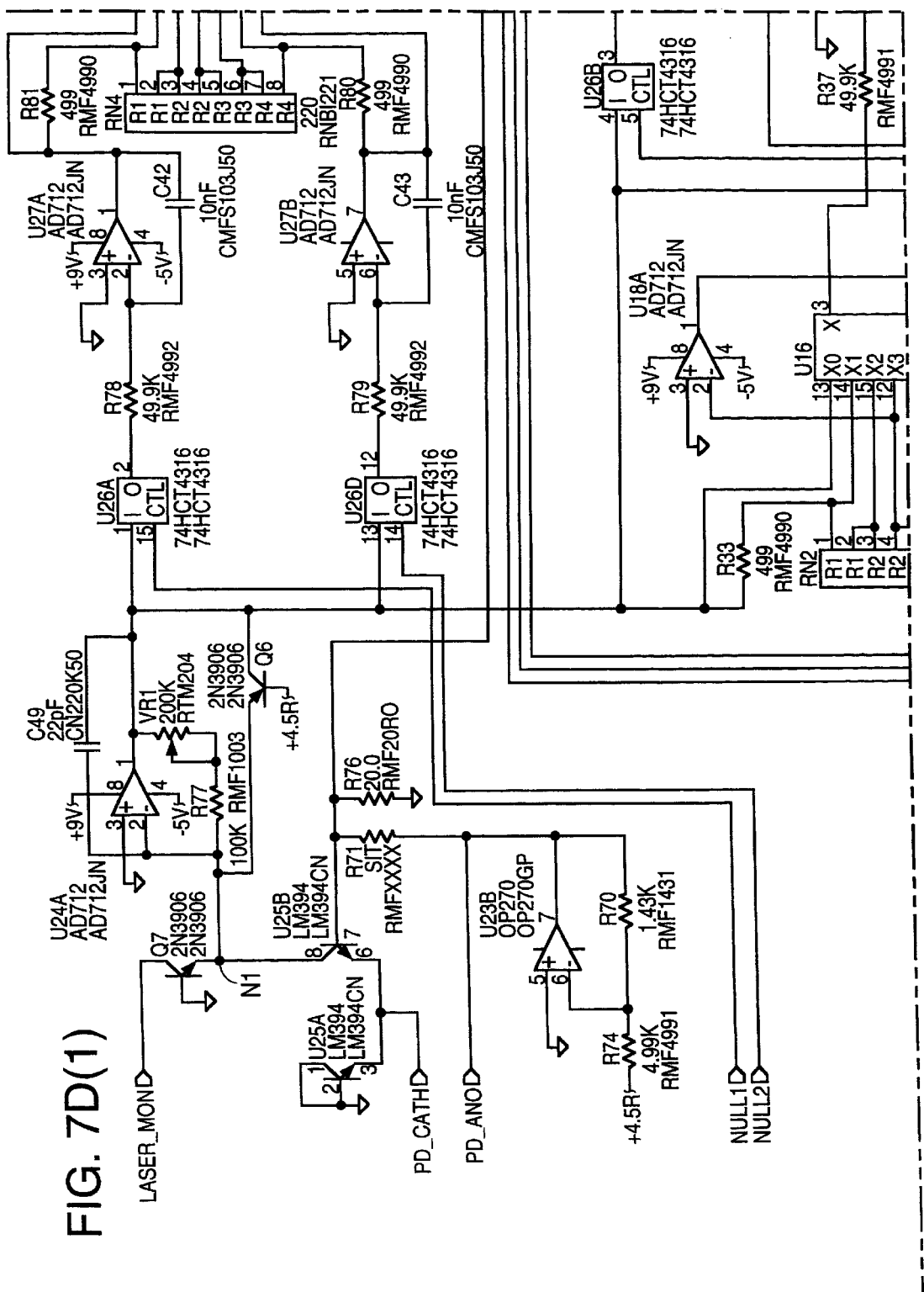
FIG. 7D(1)

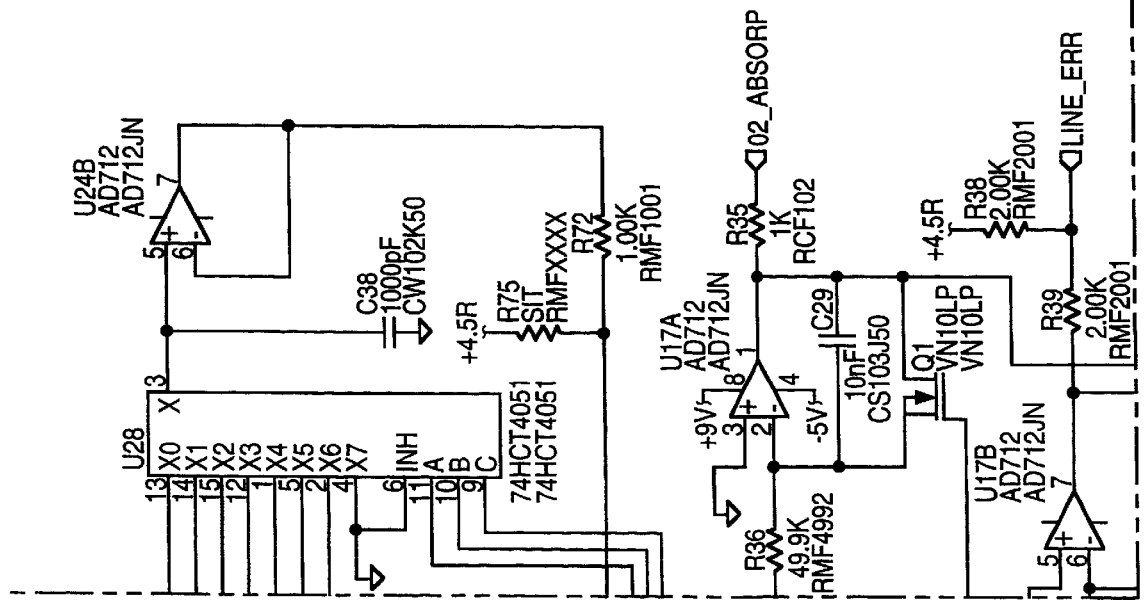
FIG. 7D(2)

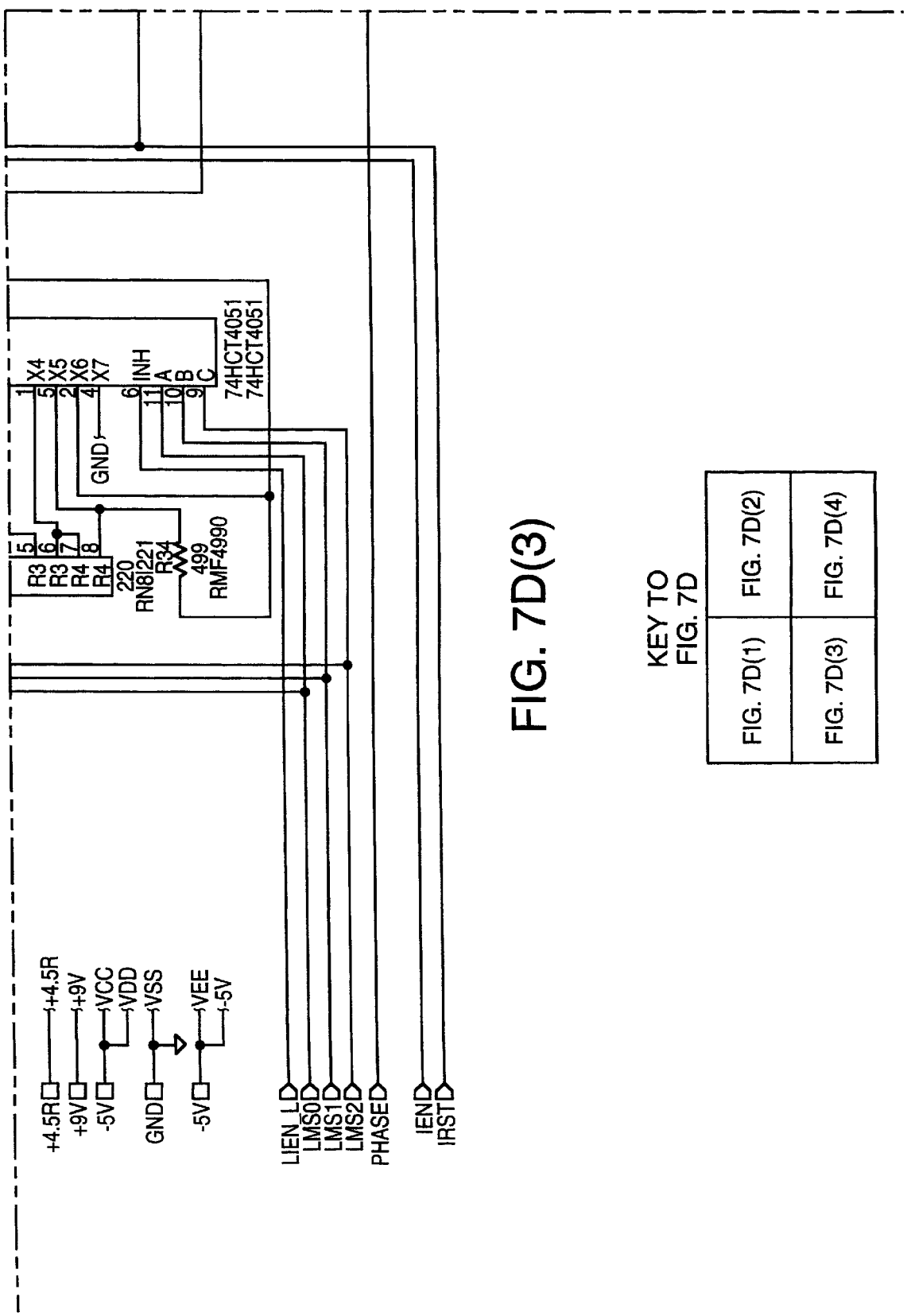
FIG. 7D(3)

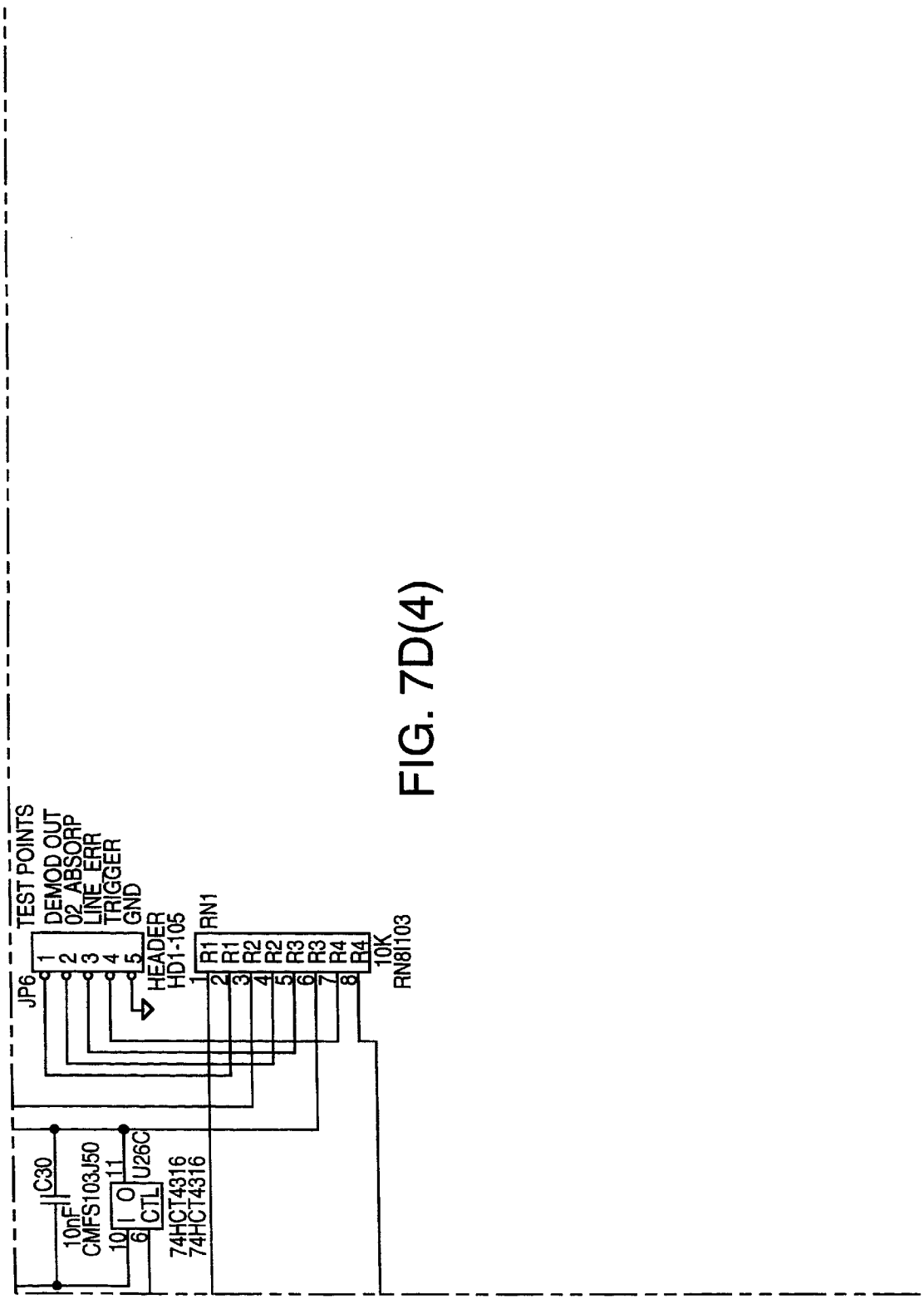

GAS SPECTROSCOPY

This application is a continuation division of application Ser. No. 08/049,474, filed Apr. 16, 1993, now U.S. Pat. No. 5,448,071.

CROSS REFERENCE TO MICROFICHE APPENDIX

The microfiche appendix, which is a part of the present disclosure, comprises 1 sheet of microfiche having a total of 44 frames. The microfiche appendix is a listing of software executable in the microcontroller U3 of the spectroscopy device represented by the detailed schematic of FIGS. 7A–7G.

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights.

FIELD OF THE INVENTION

This invention relates to absorption spectroscopy. More particularly, this invention relates to the detection of oxygen concentration in human breath using a laser diode as a source of laser radiation.

BACKGROUND INFORMATION

Different molecules absorb different amounts of electromagnetic radiation depending upon the frequencies of the radiation. A particular molecule therefore has a unique absorption spectrum of absorption versus radiation frequency.

FIG. 1 shows a number of absorption lines of gaseous oxygen located in the range of approximately 760 nm to 770 nm at Standard Temperature and Pressure. The relative height of the various peaks represents the relative absorption of the oxygen. Taller peaks represent more absorption. Shorter peaks represent less absorption. The baseline represents little or no absorption.

As explained in U.S. Pat. No. 5,047,639 entitled "concentration Detector", the concentration of a component of a material under test can be detected by identifying a frequency at which the component absorbs radiation and then passing radiation of that frequency through the material and detecting the amount of radiation that is absorbed. Because some molecules absorb radiation at different frequencies than do other molecules, it is often possible to isolate a characteristic absorption line of a particular component of interest in the material under test from the absorption lines of other components in the material under test. The detection of more radiation absorption indicates a higher concentration of the component of interest. The detection of less radiation absorption indicates a lower concentration of the component of interest.

In absorption measurements of gas concentrations using laser diode sources, the current supplied to the laser diode is typically dithered using a sinusoidal, triangular, or some other continuously cyclical perturbation of the laser diode current which causes wavelength modulation (WM) of the resulting laser radiation. Cyclical perturbation allows use of phase-sensitive harmonic detection methods both to center the modulation around the absorption line of interest and to measure the absorption strength. The first or third harmonic of the absorption measurement gives an asymmetric signal with a zero at line center useful for centering the radiation on the absorption line of interest. The second harmonic is symmetric about the absorption line thereby providing an amplitude which is proportional to absorption. Because the signal used to detect absorption occurs at twice the modulation frequency, the higher frequency absorption signal may be filtered from electrical and/or optical noise which occurs at the lower modulation frequency.

Another method of measuring absorption using laser diodes is called frequency-modulation (sometimes called FM spectroscopy). In FM spectroscopy, the modulation frequency is higher than the frequency half-width of the absorption line being measured. For narrow gas absorption lines this may require GHz modulation frequencies, but these high frequencies are free of excess low-frequency laser noise. By using two closely spaced modulation frequencies (two-tone FMS), signal processing at a more convenient MHz beat frequency is possible. As in wavelength modulation spectroscopy, phase-sensitive detection can be used. Little attention is usually given to the acquisition and maintenance of the absorption line at the center of the laser device modulation.

Another issue commonly discussed in the prior art literature is etalon effects which are created by windows and/or other parallel reflecting surfaces in the optical path. "Frequency Modulation and Wavelength Modulation Spectroscopies: Comparison of Experimental Methods Using a Lead-salt Diode Laser," by D. S. Bomse, A. C. Stanton and J. A. Silver, in Applied Optics, Vol. 31, No. 6, Feb. 20, 1992 and U.S. Pat. No. 4,934,816 entitled "Laser Absorption Detection Enhancing Apparatus and Method", issued to J. A. Silver and A. C. Stanton on Jun. 19, 1990 describe a fringe reduction technique where optical elements are vibrated mechanically at 30 Hz so that the fringes will be averaged by the high frequency and/or will be reduced by narrow band detection techniques.

Other sources of noise are also important. At low frequencies, randomly scattered light reentering the laser, drive current fluctuations, laser amplitude noise, laser frequency noise, detector noise, and amplifier noise are problems. The conventional solutions to these noise problems comprise the narrow band detection and frequency shifting techniques described above.

SUMMARY OF THE INVENTION

In contrast to the continuously varying waveforms of the prior art, a stepped laser diode drive current waveform is supplied to a laser diode in accordance with one aspect of the present invention. The use of this stepped laser drive current waveform generally sacrifices the possibility of phase-sensitive lock-in detection, the possibility of shifting of detection frequencies to second and higher order harmonics, and the possibility of shifting detection frequencies to high frequencies away from low frequency noise.

In accordance with one embodiment of the present invention, the stepped laser diode drive current waveform is a periodic waveform, each period comprising a series of constant current intervals. Each of the constant current intervals may, for example, be approximately 0.1 ms to 10 ms in duration. The laser diode drive current is switched from one constant current to the next constant current in a current switching episode having a much shorter time, for example, 0.1 us to 10 us. The detection of absorbance may be disabled during the current switching episodes when noise may be introduced due to switching transients.

By detecting absorption during the constant laser diode current intervals, the functions of subtracting baseline noise, centering radiation frequencies on the absorption line, and measuring the absorbance at the peak frequency of the absorption line can be separated. The separation of these different functions allows, for example, a larger proportion of the time to be spent integrating absorption line absorbance at the peak of the absorption line and a smaller proportion of the time to be spent performing overhead activities such as detecting baseline absorbance and centering the laser radiation frequencies on the absorption line of interest. By detecting baseline absorption several linewidths away from the peak of the gas absorption line, and by using two radiation detectors, one which detects radiation which passes through the gas sample and the other which detects radiation which does not pass through the sample, baseline absorption measurements can be subtracted from the absorption measurement at the peak of the spectral line.

In some embodiments, the amount of time spent measuring absorbance at the absorption line peak versus the amount of time spent performing overhead activities during each period of the stepped waveform is varied dynamically by changing the duration of the various intervals comprising the stepped waveform. Also, in measuring gas concentrations at various atmospheric pressures, changes in barometric or pneumatic circuit pressure alter absorption line linewidth. By detecting gas pressure, the durations of the constant current intervals can be adjusted to compensate for pressure dependent line broadening effects.

In accordance with one aspect of the present invention, a baseline nulling circuit equalizes a differential radiation detection circuit so that the differential radiation detection circuit outputs a signal indicating changes in detected sample cell radiation with respect to detected baseline radiation. The nulling circuit detects baseline radiation during baseline intervals where the frequency of the laser radiation is several linewidths away from the absorption peak. Accordingly, baseline noise and/or drifts such as slowly-varying etalon effects are canceled once every multi-interval detection period of the stepped waveform at, for example, a 0.1 to 10 KHz rate, thereby making mechanical dithering elements of the prior art unnecessary.

In accordance with another aspect of the present invention, the differential radiation detection circuit performs common mode noise cancellation. This differential radiation detection circuit cancels common mode noise, such as laser current noise, which is common both in a reference channel as well as in a sample channel. In one embodiment, the differential radiation detection circuit cancels common mode noise of frequencies up to approximately 100 MHz. The differential radiation detection circuit preferably performs this noise cancellation during both baseline and peak intervals.

In accordance with another aspect of the present invention, autoranging software or dual-slope integration may be used to increase absorption measurement resolution.

Aspects of this invention may be used in determining the absorbance, refraction, fluorescence, temperature, and/or pressure of air (or any material which absorbs wavelengths and absorption linewidths similar to laser diode emission wavelengths and emission linewidths). Aspects of the present invention may also be used in the determination of the range to an object in air or another material.

In accordance with another aspect of the present invention, a spectroscopy device is disclosed comprising a line locking cell as well as a sample cell. Even when little or no material is present in the sample cell which has the absorption spectral line of interest, the spectroscopy device is able to lock onto an amount of the absorption material in the line locking cell. A spectroscopy device in accordance with one embodiment of the present invention can measure oxygen concentrations in a sample cell anywhere from 100 percent down to 0 percent. The sample cell and an input tube are heated to prevent condensation inside the sample cell when human breath or any humidified sample is introduced through the input tube and into the sample cell. The temperature and pressure of the contents of the sample cell are detected in order to compensate absorption measurements for pressure and temperature absorption dependencies. The line locking cell and the sample cell are disposed serially to reduce the complexity of the device, to reduce cost, and to yield a compact device. A laser diode/lens assembly is used rather than a conventional collimator to further reduce cost. A photodetector holding member is provided which reduces the amount of laser radiation which is reflected back through the sample cell off the photodetector.

In accordance with still other embodiments of the present invention, structures and techniques involving angling surfaces which may otherwise cause unwanted reflections, focussing the beam of laser radiation at a point inside the sample away from a possibly reflective surface, introducing a quarter wave plate into the laser diode to sample cell optical path, and introducing a neutral density absorber into the laser diode to sample cell optical path are disclosed. An evanescent wave on-airway structure usable to pass laser radiation through the breath of a patient is also disclosed.

BRIEF DESCRIPTION OF THE DRAWINGS

FIGS. 7A–7G comprise a more detailed schematic diagram of the oxygen detector described above in connection with the simplified schematic of FIG. 5 and the timing diagram of FIG. 6.

FIG. 20 illustrates an evanescent wave traveling in a section of optical fiber.

DESCRIPTION OF THE PREFERRED EMBODIMENTS

The frequency (and therefore wavelength) of the radiation emitted from a laser diode-chip is dependent upon the physical dimensions of the laser diode chip as well as the current density through the laser diode chip. Because the size of a laser diode chip is temperature dependent, the wavelength of radiation emitted from a laser diode chip can be varied by varying the temperature of the laser diode chip.

Figure 1:
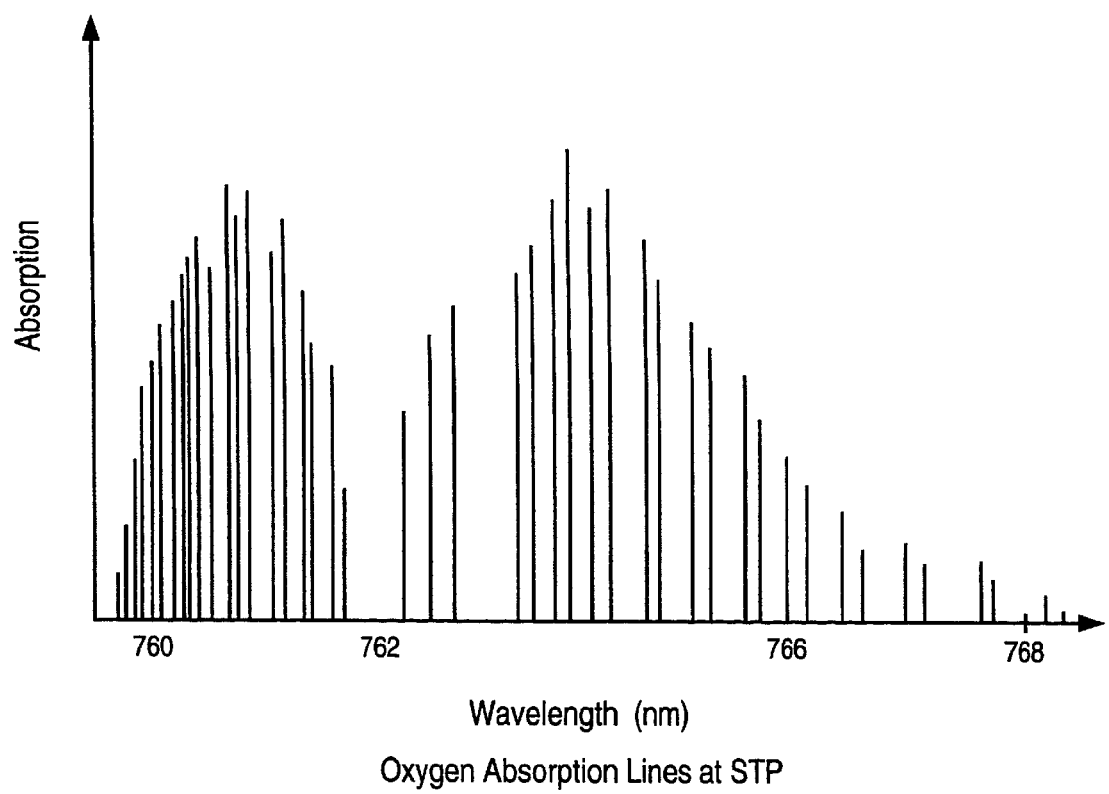
FIG. 1 is a diagram showing a number of absorption lines located in the range of approximately 760 nm to 770 nm for gaseous oxygen at Standard Temperature and Pressure.
Figure 2:
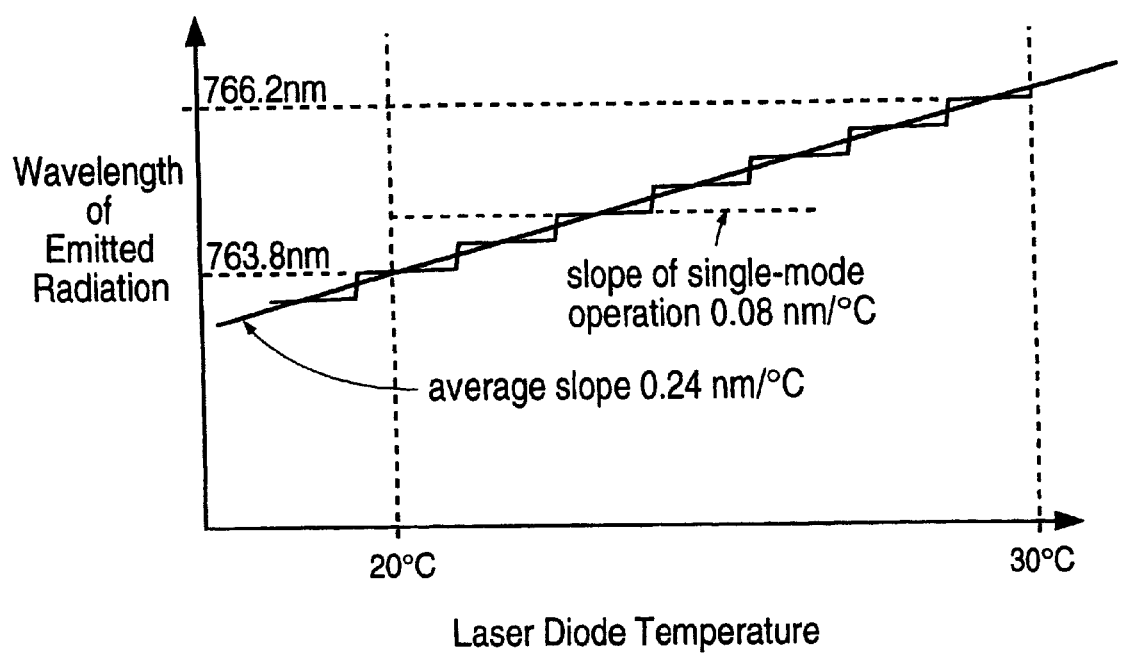
FIG. 2 is a diagram illustrating the wavelength of radiation generated by a laser diode versus temperature of the laser diode.

FIG. 2 is a diagram illustrating the wavelength of radiation generated by a laser diode versus temperature of the laser diode. The wavelength to temperature relationship, rather than being a linear relationship, has a stepped characteristic. As illustrated in FIG. 2, the wavelength of the emitted laser radiation increases gradually over some temperature ranges whereas the wavelength of the emitted laser radiation jumps in wavelength over other, relatively smaller, temperature ranges. The jumps in wavelength are called mode hops because the wavelength of the radiation emitted from the laser diode "hops" from one wavelength to another. A region of operation between two successive mode hops is called a "single mode" operating region.

In order to generate laser radiation, an integral number of half waves of radiation must be reflected within the laser diode chip between two reflective surfaces of the laser diode chip. When the optical path length of a laser diode chip is changed within a single mode operating region, the wavelength of the emitted laser radiation increases gradually with the change in laser diode optical dimension while the integral number of half waves reflected inside the laser diode does not change. When the dimensions of the laser diode chip is changed over a mode hop, however, the integral number of half waves suddenly changes thereby producing the hop in wavelength.

Because individual laser diodes typically are manufactured having slightly different physical dimensions at a given laser diode temperature, the wavelengths at which a number of laser diodes will experience mode hops typically varies from laser diode to laser diode. A spectral absorption line of a material which happens to occur at a wavelength corresponding with the wavelength of a mode hop of a particular laser diode will result in the particular laser diode not being able to produce laser radiation of the proper wavelength corresponding to that spectral line. A small change in temperature will result in the particular laser diode generating laser radiation which skips over the spectral line.

Furthermore, a laser diode chip typically has a region of operation in which the laser radiation produced is not monochromatic. Two or more wavelengths of laser radiation may be simultaneously produced. This is known as "multi-modal" operation. Moreover, the temperatures at which such multi-mode laser diode operation occurs can change over the lifetime of a laser diode.

Despite the above-described problems associated with laser diodes, the present invention nevertheless uses a laser diode to generate a highly monochromatic source of radiation which is tunable to the wavelength of a spectral absorption line of a material under analysis. In, for example, the spectroscopic determination of concentration of oxygen, multiple relatively weak and narrow oxygen spectral absorption lines exist in the range of 760 nm to 770 nm at Standard Temperature and Pressure. Typical absorption of one of the stronger lines over a few inch path length in 100 percent $O_2$ is less than one percent. The width of such a spectral line is typically only about 4 pm. Although some of these oxygen absorption spectral lines may occur at the same wavelengths as the mode hops of a given laser diode, other of the oxygen absorption spectral lines generally will occur at different wavelengths where no mode hop exists.

One particular oxygen absorption spectral line is therefore chosen for the individual laser diode chip of each individual oxygen concentration spectroscopy device. The particular oxygen absorption spectral line chosen is a preferably strong absorption peak which is well separated from any neighboring absorption peaks and which is located in a single mode region of the particular laser diode away from the edges of a single-mode region of the laser diode. The emitted radiation from the particular laser diode can therefore be scanned in wavelength both above and below the wavelength of the particular spectral line chosen without leaving the single-mode operating region. This allows for future adjustment of the oxygen detector spectroscopy device over product lifetime.

To determine the particular oxygen absorption spectral line for a particular laser diode, the wavelength of the laser radiation emitted from the particular laser diode is scanned during device manufacture from single-mode operating region to single-mode operating region until a suitable spectral line is found. Because operation of a laser diode at a low power can cause the laser diode to exhibit multi-modal behavior and because operation of a laser diode at a very high power can cause the wavelengths of the mode hops to shift over laser diode lifetime, the laser diode is operated within maximum and minimum power range both during manufacture or during normal operation. For the type of laser diode having the characteristic represented in FIG. 2, operation at powers less than 1 mW commonly results in multi-modal radiation being emitted.

Figure 3:
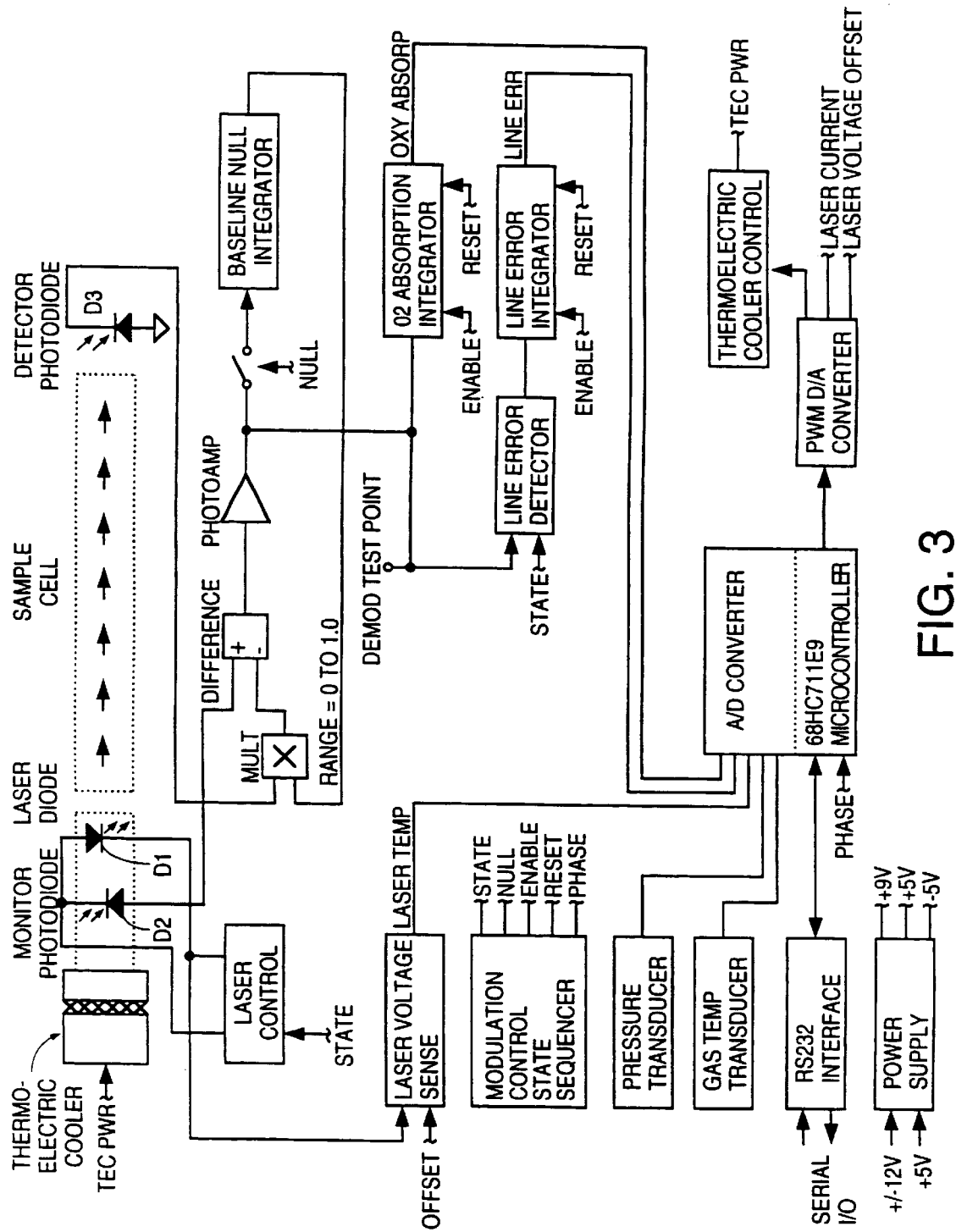
FIG. 3 is simplified block diagram of an oxygen concentration spectroscopy device in accordance with one embodiment of the present invention.

FIG. 3 is a simplified block diagram of an oxygen concentration spectroscopy device in accordance with one embodiment of the present invention. A laser diode D1 emits a beam of laser radiation through a sample cell containing a sample of gas. The concentration of oxygen in the sample gas is to be measured. A monitor photodetector, for example a photodiode, D2 is used to generate a signal indicative of the magnitude of the laser radiation supplied into the sample cell. A single photodetector, for example a photodiode, D3 is used to generate a signal indicative of the magnitude of the laser radiation which is transmitted through the gas in the sample cell. Using the monitor photodiode D2 as a reference, the oxygen concentration spectroscopy device determines the relative amount of laser radiation which is absorbed by the gas in the sample cell.

A coarse adjustment of laser radiation wavelength is performed by coarsely controlling the temperature of the package or housing containing the laser diode. The temperature of the laser diode housing is cooled with thermoelectric coolers to the approximate laser diode temperature desired. The temperature of the laser diode housing is measured either by a thermistor in close thermal contact with the laser diode housing or by measuring the magnitude of the temperature-dependent forward voltage drop of the laser diode itself. Because the laser diode housing and the associated sample cell assembly has a relatively long thermal time constant, the control loop for cooling of the laser diode package via the thermoelectric coolers has a relatively slow response.

Fine adjustment of laser radiation wavelength is performed by controlling the laser diode drive current supplied to the laser diode chip itself. Larger drive currents result in increased power dissipation of the laser diode chip. This results in increased laser diode gain and chip temperature. In contrast to the slow response time of the thermoelectric cooler control loop, the laser diode drive current control loop has a relatively fast response.

Because the absorption lines of oxygen are so narrow, it is generally not possible to tune the laser radiation to the peak absorption wavelength of a desired spectral absorption line and to forever thereafter measure absorption through the sample cell. The wavelength of the radiation emitted from the laser diode is therefore frequently adjusted to keep the laser diode radiation "locked" onto the spectral absorption line of interest.

Figure 4A:
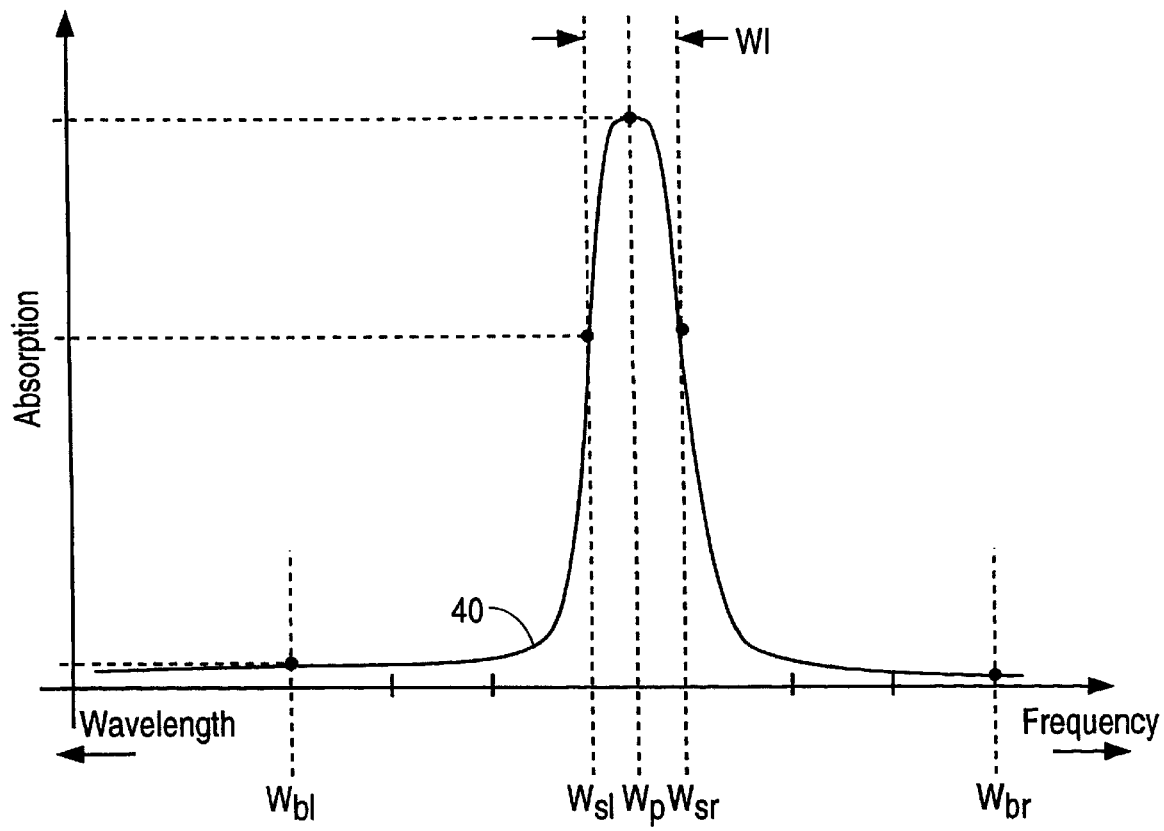
FIG. 4A is a diagram illustrating a spectral absorption line of oxygen when the oxygen concentration spectroscopy device of FIG. 3 is "locked" onto the spectral absorption line.

FIG. 4A is a diagram illustrating a spectral absorption line 40 in relation to the operation of the oxygen concentration spectroscopy device of FIG. 3 when the oxygen concentration spectroscopy device is "locked" onto the spectral absorption line 40. The spectral absorption line illustrated in FIG. 4A is drawn having an exaggerated width WI for illustration purposes. The laser diode D1 of FIG. 3 is controlled to emit laser radiation of five different wavelengths: a left baseline wavelength $w_{bl}$, a left skirt wavelength $w_{sl}$, a peak wavelength $w_p$, a right skirt wavelength $w_{sr}$, and a right baseline wavelength $w_{br}$. The left baseline wavelength $w_{bl}$ is located several linewidths lower in frequency than is the left skirt wavelength $w_{sl}$. Similarly, the right baseline wavelength $w_{br}$ is located several linewidths higher in frequency than is the right skirt wavelength $w_{sr}$. The baseline wavelengths $w_{bl}$ and $w_{br}$ are generated to determine the relative amount of radiation which passes through the sample cell with little or no absorption in the sample cell versus the amount of radiation introduced into the sample cell. The skirt wavelengths $w_{sl}$ and $w_{sr}$ are generated to determine the degree to which the peak wavelength $W_p$ of the radiation emitted from the laser diode differs from the actual wavelength of the peak of the absorption line. The difference between the peak wavelength $W_p$ generated by the oxygen concentration detector and the wavelength of the peak of the actual spectral line is called the line lock error.

In FIG. 4A, the magnitudes of the absorption at the left skirt wavelength $w_{sl}$ and the right skirt wavelength $w_{sr}$ do not differ from one another so the oxygen concentration detector is said to be "locked" onto the absorption line 40.

The peak wavelength $W_p$ is generated so that the magnitude of the radiation detected to have passed through the sample cell at the peak wavelength $w_p$ can be subtracted from the magnitude of the radiation detected to have passed through the sample cell at the baseline wavelengths and $w_{bl}$ $w_{br}$ to generate a measure of radiation absorbed in the sample cell.

Figure 4B:
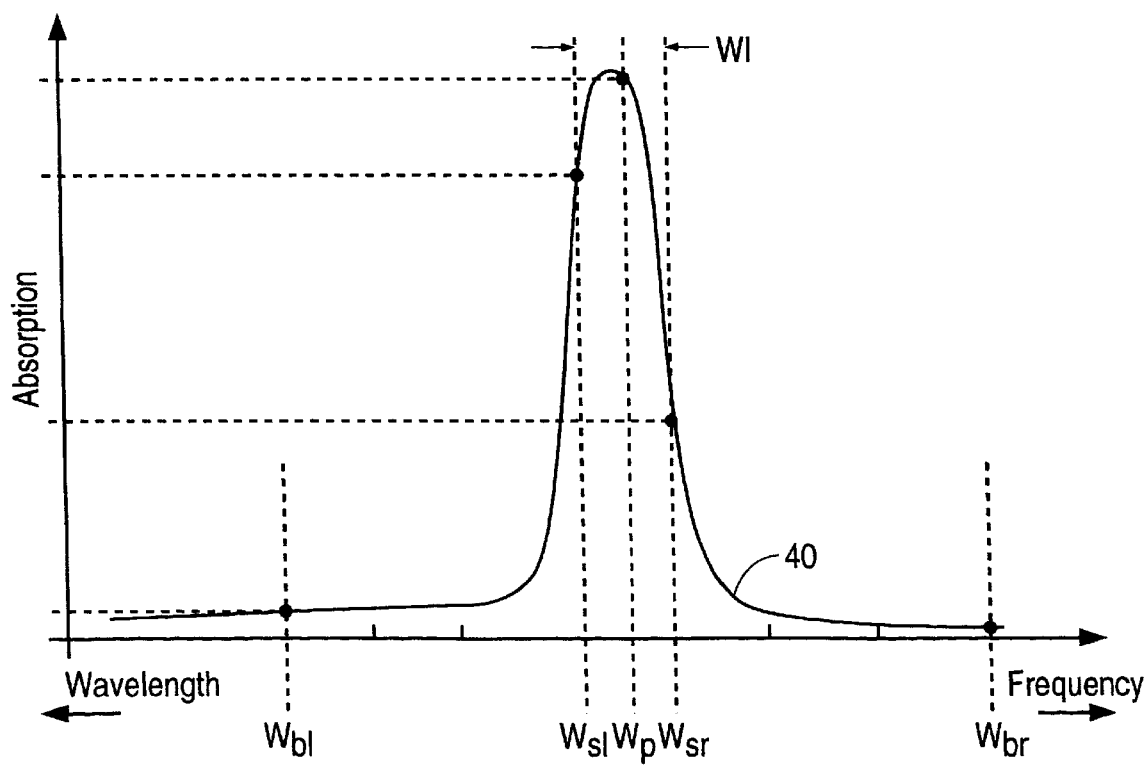
FIG. 4B is a diagram illustrating a spectral absorption line of oxygen when the oxygen concentration detector of FIG. 3 is generating a lock error signal caused by an imbalance in $w_{sl}$ and $w_{sr}$.

FIG. 4B is a diagram illustrating a spectral absorption line 40 in relation to the operation of the oxygen concentration detector of FIG. 3 when the oxygen concentration detector is not perfectly "locked" onto the spectral absorption line 40. If the magnitudes of the radiation detected at the left and right skirt wavelengths differ from one another as illustrated in FIG. 4B, then the peak wavelength of the actual spectral line is determined not to be centered between the two skirt wavelengths. The baseline, skirt and peak wavelengths in FIG. 4B should be shifted downward in frequency to achieve optimal line lock.

The simplified block diagram of FIG. 3 illustrates how the radiation detected at the baseline wavelengths can be subtracted from the radiation detected at the peak and skirt wavelengths so that the results are indicative of the skirt and peak absorbances of the material in the sample cell. A difference circuit labeled DIFFERENCE detects the difference in current between its two inputs leads. The current from the monitor photodetector D2 is supplied to one of the input leads of this difference circuit. The current from the detector photodiode D3 is, however, not supplied directly to the difference circuit. Rather, the current from the detector photodiode D3 is supplied to an input lead of a multiplier circuit labeled MULT and the output of the multiplier circuit MULT supplies the current to the second input lead of the difference circuit.

In operation, there are five basic time intervals. During a first time interval, the left baseline wavelength $w_{bl}$ is generated; during a second time interval the left skirt wavelength $w_{sl}$ is generated; during a third time interval the peak wavelength $w_p$ is generated; during a fourth time interval the right skirt wavelength $w_{sr}$ is generated; and during a fifth time interval the right baseline wavelength $w_{br}$ is generated. During the baseline wavelength time intervals, a null switch is closed by the signal labeled NULL. A baseline null integrator controls the second input lead of the multiplier circuit so that the magnitude of the current supplied to the second input lead of the difference circuit from the signal photodetector D3 exactly equals the magnitude of the current supplied to the first input lead of the difference circuit from the monitor photodetector D2. After the baseline interval, the null switch is opened so that the baseline null integrator will maintain this condition during the skirt and peak time intervals when the absorption at the skirt and peak wavelengths is detected. As a result, the difference between the monitor photodetector current during the baseline intervals and the signal photodetector current during the measurement of sample cell absorption at the skirt and peak wavelengths is detected.

If oxygen is present in the sample cell during skirt and peak intervals, the voltage of the signal output from the photoamplifier labeled PHOTOAMP will be negative during the skirt and peak intervals. This voltage signal is integrated by the circuit labeled $O_2$ ABSORPTION INTEGRATOR to derive an unscaled output signal OXY_ABSORP. OXY_ABSORP is indicative of the amount of oxygen absorption due to the spectral line. Integration is used, rather than simple sampling of the peak photoamplifier output, in order to provide noise reduction. The magnitude of the signal OXY_ABSORP is read by an on-chip A/D converter of a Motorola 68HC711E9 microcontroller. The microcontroller determines a percent oxygen based on the value of the OXY_ABSORP signal.

A measure of the line lock error is required to maintain the radiation of the laser diode locked onto the absorption line of interest. The line error detector labeled LINE ERROR DETECTOR in FIG. 3 inverts the magnitude of the voltage signal output from the photoamplifier PHOTOAMP during the right skirt interval. Both the non-inverted left skirt photoamplifier voltage output and inverted right skirt photoamplifier voltage output are integrated by a line error integrator circuit labeled LINE ERROR INTEGRATOR in FIG. 3. The output of the line error integrator after both the left and right skirt intervals is integrated is a measure of the line lock error. The microcontroller reads the integrated line lock error signal LINE_ERR via the A/D converter and adjusts the laser diode drive current and/or thermoelectric cooler current to adjust the wavelengths $w_{bl}$, $w_{sl}$, $w_p$, $w_{sr}$ and $w_{br}$ in order to correct those wavelengths with respect to the actual wavelength of the peak of the absorption line.

When the oxygen concentration spectroscopy device is first turned on, the wavelengths of the laser radiation emitted from the laser diode are forced to the particular absorption line preselected for operation during device manufacture. The forward voltage drop across the laser diode is therefore detected by a laser voltage sense circuit labeled LASER VOLTAGE SENSE in FIG. 3 and the signal output from the laser voltage sense circuit is read by the microcontroller as an indication of laser diode temperature. The microcontroller uses the signal output from the laser voltage sense circuit as a measure of laser diode temperature so that the microcontroller can control laser diode temperature through the thermoelectric coolers and laser diode drive current such that laser radiation of wavelengths corresponding to the preselected spectral line are generated. In some embodiments, a thermistor disposed in thermal contact with the housing of the laser diode is used by the microcontroller to detect laser diode temperature.

Figure 5:
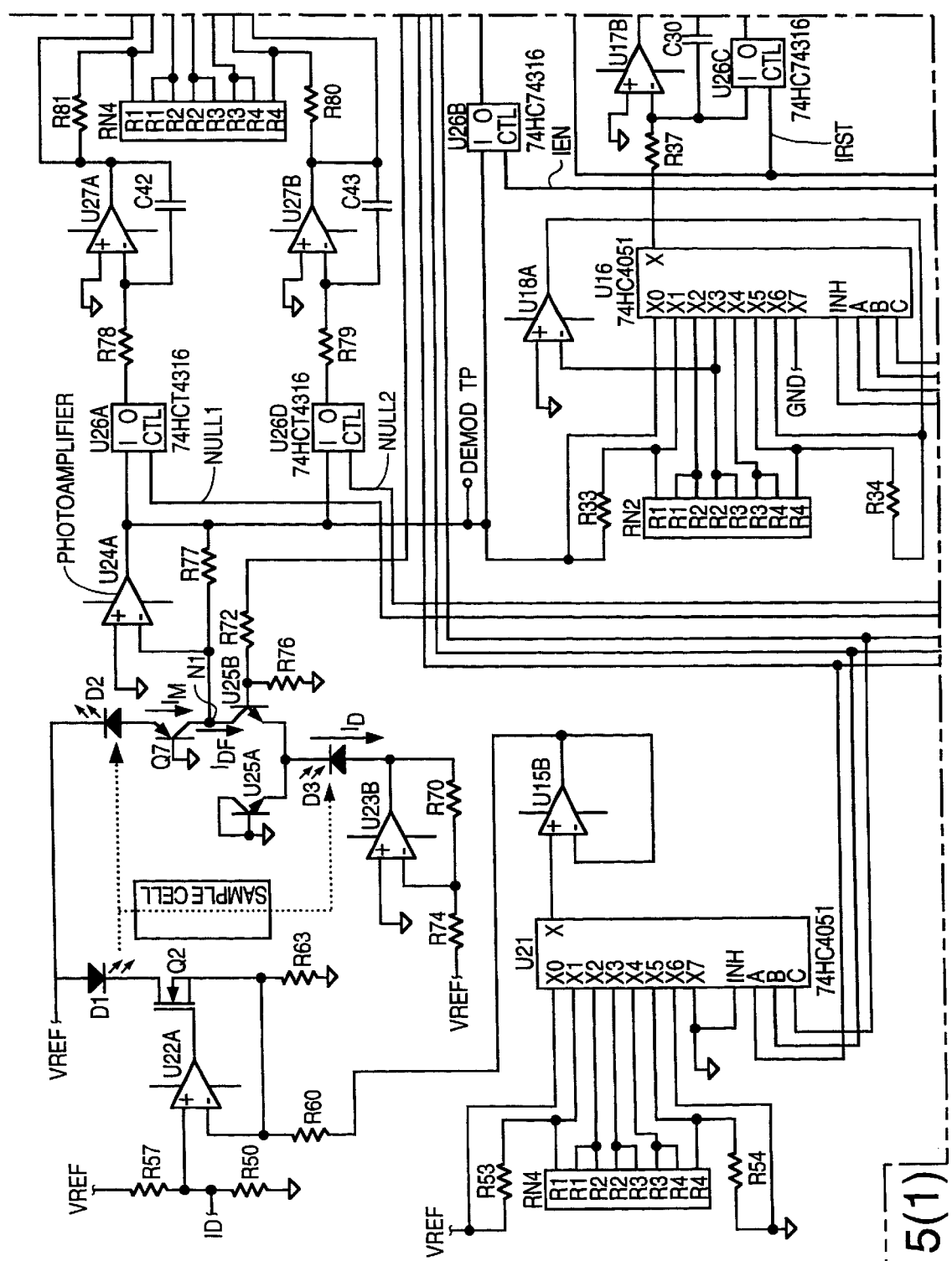
FIG. 5 is a simplified schematic corresponding with the simplified block diagram of FIG. 3.
Figure 5:
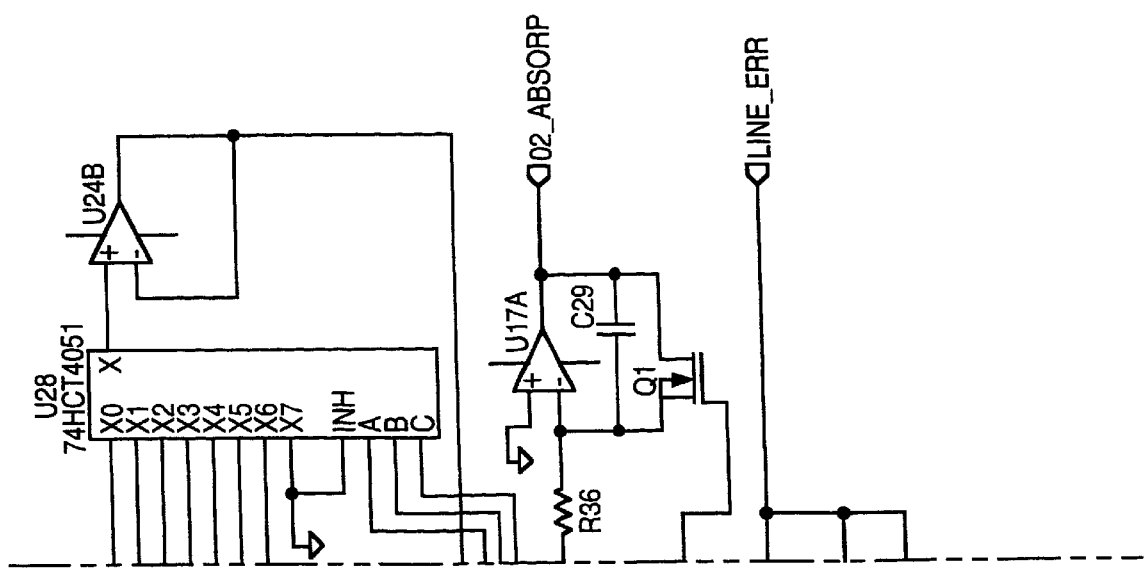
Figure 5:
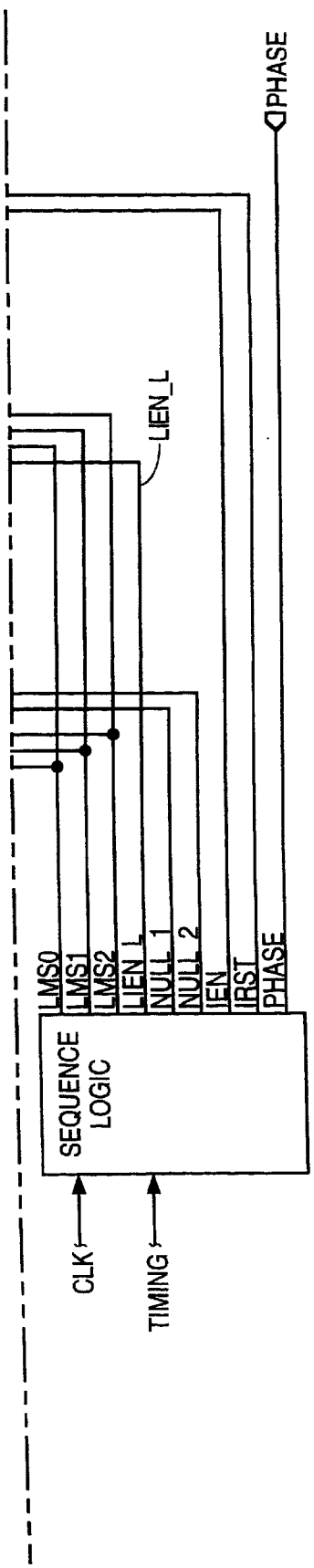

FIG. 5 is a simplified schematic corresponding with the simplified block diagram of FIG. 3. This simplified schematic also corresponds with the detailed schematic of FIGS. 7A–7G. The individual baseline, skirt and peak intervals may be of too short of time durations for the microcontroller to monitor and control. Consequently, a sampling modulation control state sequencer labeled SEQUENCE LOGIC in FIG. 5 is provided to generate various control signals which control the oxygen concentration spectroscopy device circuitry. The microcontroller (not shown on FIG. 5) is synchronized to the sequencer via the PHASE signal which is generated by the sequencer.

Figure 6:
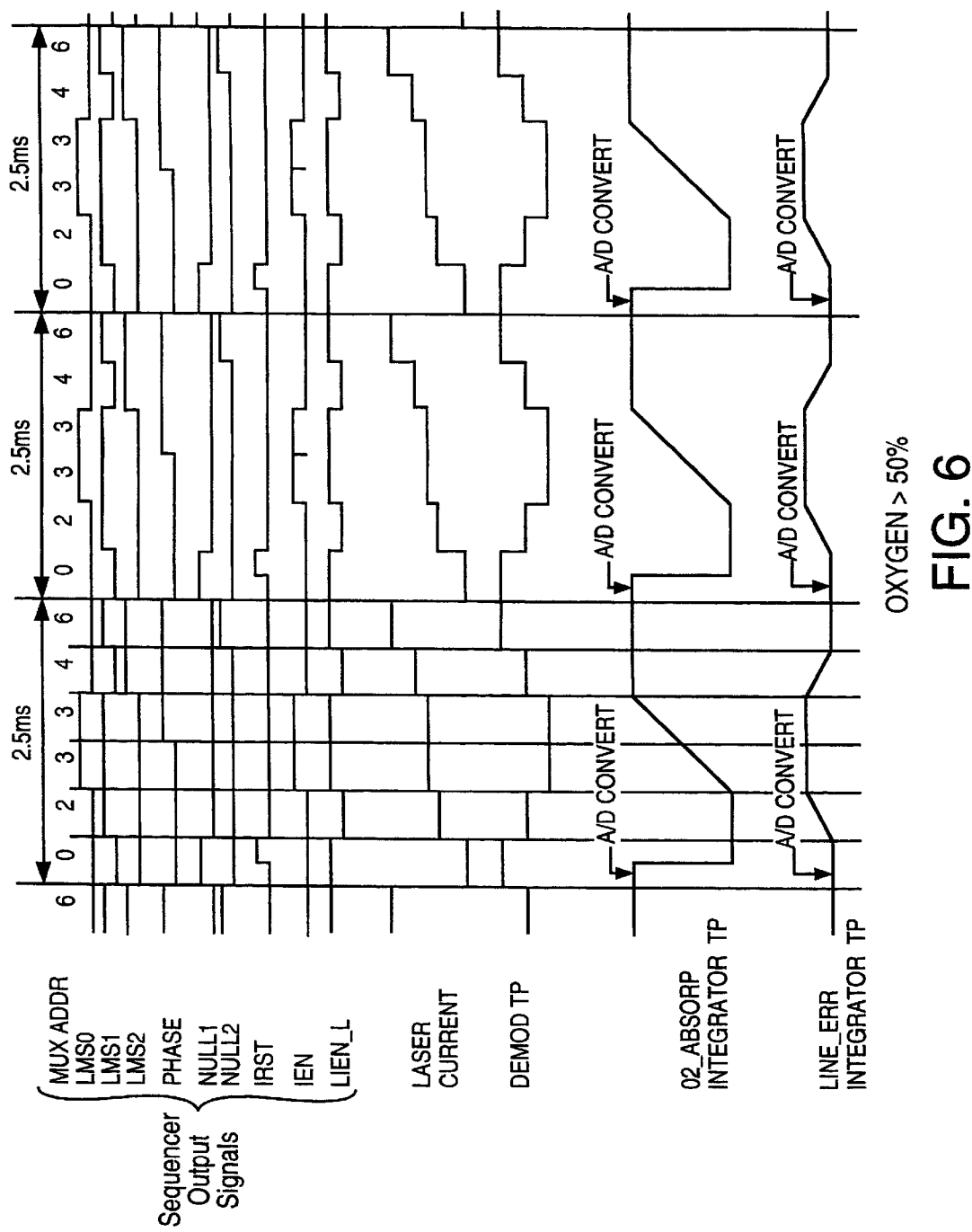
FIGS. 6, 6A and 6B illustrate waveforms associated with the operation of the circuit of the simplified schematic FIG. 5.

FIG. 6 illustrates various waveforms associated with the operation of the circuit of the simplified schematic of FIG. 5 and the detailed schematic of FIGS. 7A–7G. A laser diode drive current flows through laser diode D1 and to a current sink comprising operational amplifier U22A and MOS transistor Q2. The DC component of the laser diode drive current is set by resistors R57 and R58, and is controlled by microcontroller U3 through signal ID and series resistor R56. Signal ID sets the laser drive current to about 40 mA whereas U22A and Q2 vary the drive current by an additional 0 to 2 mA. The laser diode drive current is varied over time through the five constant current interval sequence of the waveforn labeled LASER CURRENT in FIG. 6 by injecting current through resistor R60 from operational amplifier U15B. The voltage output from operational amplifier U15B is varied under sequencer control by scanning the address inputs of the analog multiplexer U21 so that the taps of a resistor voltage divider comprising resistors R53, RN3, and R54 are sequentially connected to the output lead X of the analog multiplexer U21. The analog multiplexer U21 selects taps X0, X2, X3, X4, and X6 in a periodic sequence controlled by address inputs LMS0, LMS1, and LMS2. The timing diagram of FIG. 6 shows the address inputs LMS0, LMS1 and LMS2 scanning through the corresponding MUX ADDR values 0, 2, 3, 4, 6 in a repeating fashion so that the stepped laser diode current waveform labeled LASER CURRENT having five intervals per period is generated. The peak interval (MUX ADDR of 3) is of longer duration than are the baseline (MUX ADDR of 0 and 6) and skirt intervals (MUX ADDR of 2 and 4).

As illustrated in FIG. 5, monitor photodiode D2 detects laser radiation emitted from laser diode D1 before the laser radiation passes through the sample cell. Signal photodiode D3, however, detects laser radiation which has passed through the sample cell. The current $I_M$ flowing through monitor photodiode D2 passes through bipolar transistor Q7 to node N1. The current $I_D$ conducted by signal photodiode D3 to the current sink comprising operational amplifier U23B and resistors R74 and R70 is supplied by the combination of matched bipolar transistors U25A and U25B. The fraction of signal photodiode current $I_D$ that comes from U25B is determined by the voltage difference between the bases of the transistor pair U25A and U25B. The voltage on the base of bipolar transistor U25B is controlled by the left and right baseline null integrator circuits comprising resistors R76, R72, operational amplifier U24B, analog multiplexer U28, resistor voltage divider R81, RN4, and R80, operational amplifiers U27A, U27B, capacitors C42 and C43, resistors R78 and R79, and analog switches U26A and U26D.

During the left baseline interval, switch U26A is closed. LMS0, LMS1 and LMS2 address the analog multiplexer U28 as illustrated in FIG. 6 such that multiplexer input X0 connects the output from operational amplifier U27A to multiplexer output X. The integrator comprising operational amplifier U27A, resistor R78, and capacitor C42 therefore integrates the voltage on the output of photoamplifier U24A such that the magnitude of the fractional current $I_{DF}$ flowing from node N1 through bipolar transistor U25B is equalized to be substantially equal to the magnitude of the current $I_M$ flowing into node N1 from monitor photodiode D2.

This left baseline interval is illustrated in FIG. 6 as the interval underneath MUX ADDR 0. Analog switch U26A is controlled by signal NULL1 which is in turn generated by the sequencer. As illustrated in FIG. 6, signal NULL1 is low during all intervals other than the left baseline interval. Accordingly, analog switch U26A is opened at the end of the left baseline interval and the integrator comprising operational amplifier U27A and capacitor C42 stops integrating and holds the value integrated until the analog switch U26A is again opened.

The right baseline null integrator operates in a similar fashion. During the right baseline interval, analog switch U26D is opened by the sequencer via control signal NULL2. As illustrated in FIG. 6, signal NULL2 is low during all intervals other than the right baseline interval. This right baseline interval is illustrated in FIG. 6 as the interval underneath MUX ADDR 6. During this interval, LMS0, LMS1 and LMS2 address the multiplexer U28 as illustrated in FIG. 6 such that multiplexer input X0 connects the output from operational amplifier U27B to analog multiplexer U28 output X. This equalizes the fraction of the detector photodiode current $I_{DF}$ which passes from node N1 through the bipolar transistor U25B to be equal to the monitor photodiode current $I_M$ which passes through bipolar transistor Q7 to node N1.

During the skirt and peak intervals, the fraction of the detector current $I_{DF}$ may be changed. Rather than using the fractions which equalize $I_M$ and $I_{DF}$ during the left or the right baseline intervals, respectively, bipolar transistor U25B is controlled with a weighted base voltage determined by the voltage divider comprising resistor R81, the various resistors of RN4, and resistor R80. Because resistors R81, RN4 and R80 are connected between the voltages output from the left and right integrators, the voltages output by analog multiplexer U28 during skirt and peak intervals are voltages between the voltages supplied by U27A and U27B during the left and right intervals. The voltages output from analog multiplexer U28 are therefore weighted averages of the two baseline voltages. This averaging compensates for the situation when the photoamplifier output has different voltages during left and right baseline intervals.

If, for example, the left baseline interval results in a higher base voltage on bipolar transistor U25B than does the right baseline interval, then the base voltage supplied to bipolar transistor U25B during the peak interval will be between the bipolar base voltages of the left and right baseline intervals. Due to the addressing of the analog multiplexer U28 during the successive left skirt, peak, and right skirt intervals, the left skirt interval has a bipolar transistor U25B base voltage closer to the U25B base voltage of the left baseline interval and the right skirt interval has a bipolar transistor U25B base voltage closer to the U25B base voltage of the right baseline voltage.

The voltage signal output from photoamplifier U24A is therefore indicative of the instantaneous oxygen absorption relative to the average baseline absorption. The waveform at the test point labeled DEMOD TP in FIG. 6 illustrates the voltage present on the output of photoamplifier U24A when the oxygen detector is locked to a spectral absorption line. The voltage during the left baseline interval when the MUX ADDR is 0 has the same magnitude as the voltage during the right baseline interval when the MUX ADDR is 6. The voltage on the output of photoamplifier U24A has a decreased voltage during the left and right skirt intervals having MUX ADDR values of 2 and 4, respectively. The voltage on the output of photoamplifier U24A has the lowest voltage during the peak interval when MUX ADDR value is 3. This corresponds with the greatest amount of absorbance detected in the sample cell.

Operational amplifier U17A, capacitor C29, and resistor R36 function as an oxygen absorption integrator which integrates the voltage DEMOD TP output from photoamplifier U24A. The output of this oxygen absorption integrator is illustrated in FIG. 6 as the waveform labeled O2 ABSORP INTEGRATOR TP. As illustrated in FIG. 6, the voltage of the oxygen absorption integrator is reset via signal IRST when switch Q1 shorts capacitor C29 at the beginning of each 2.5 ms measurement cycle. FIG. 6 also illustrates analog switch U26B being made conductive via signal IEN during the peak interval when MUX ADDR equals 3 in order to allow integration. During the skirt intervals and the baseline intervals, analog switch U26B is open. The voltage of O2_ABSORP INTEGRATOR TP therefore does not increase during these intervals. At the end of a 2.5 ms measurement period, the voltage O2_ABSORP INTEGRATOR TP is read by an analog-to-digital converter of microcontroller U3 as indicated in FIG. 6. The method of zeroing out the $O_2$ absorption integrator, integrating the voltage output by the photoamplifier during the peak interval, and reading the O2_ABSORP output is repeatedly performed, period and after period.

The voltage on the output lead of photoamplifier U24A which is indicative of instantaneous sample cell absorption is also processed by a line error detector. The line error detector comprises resistor R33, resistors RN2, resistor R34, analog multiplexer U16, and operational amplifier U18A. Operational amplifier U18A generates an inverted copy of the DEMOD TP waveform onto resistor R34. The resistors of RN2, R33, and R34 are connected in series to form a voltage divider between the voltage on the output of the photoamplifier to the inverted voltage on the output of the photoamplifier. One of the taps on the voltage divider is selected during each interval by analog multiplexer U16 as determined by address inputs LMS0, LMS1 and LMS2. Analog multiplexer input lead X7 is connected to a ground voltage and the sequencer maintains output signal LIEN_L at a logic high during non-skirt intervals so that the analog multiplexer U16 will connect input lead X7 to the output lead X thereby supplying ground voltage to the line error integrator comprising operational amplifier U17B, resistor R37 and capacitor C30. The result is that the line error integrator does not integrate during non-skirt intervals.

During skirt intervals, however, LIEN_L is at a logic low, thereby enabling analog multiplexer U16. The output from analog multiplexer U16 is negative during the left skirt interval, and positive during the right skirt interval due to the action of inverting operational amplifier U18A. Integrating the signal output from analog multiplexer U16 with the line error integrator operational amplifier U17B generates the line error output LINE_ERR illustrated in FIG. 6. If the magnitude of the voltage output by analog multiplexer U16 during the left skirt equals the magnitude of the voltage output by analog multiplexer U16 during the right skirt, then the integrated output LINE_ERR will be zero after both the left and right skirt intervals.

If, on the other hand, the magnitude of the voltage output by analog multiplexer U16 during the left skirt does not equal the magnitude of the voltage output by analog multiplexer U16 during the left skirt, then the integrated output LINE_ERR will not be zero after both the left and right skirt intervals. The magnitude and sign of the signal LINE_ERR at the analog-to-digital conversion illustrated in FIG. 6 is therefore indicative of the detected differences in absorption during the left and right skirt intervals. The microcontroller reads this signal LINE_ERR using its analog-to-digital converter and adjusts the thermoelectric cooler current and/or laser diode drive current based on this reading so that the absorption line in following 2.5 ms periods will be better centered between the left and right skirt wavelengths. As illustrated in FIG. 6, the line error integrator is reset by signal IRST output from the sequencer U5 during the left baseline interval at the beginning of a 2.5 ms period.

Figure 6A:
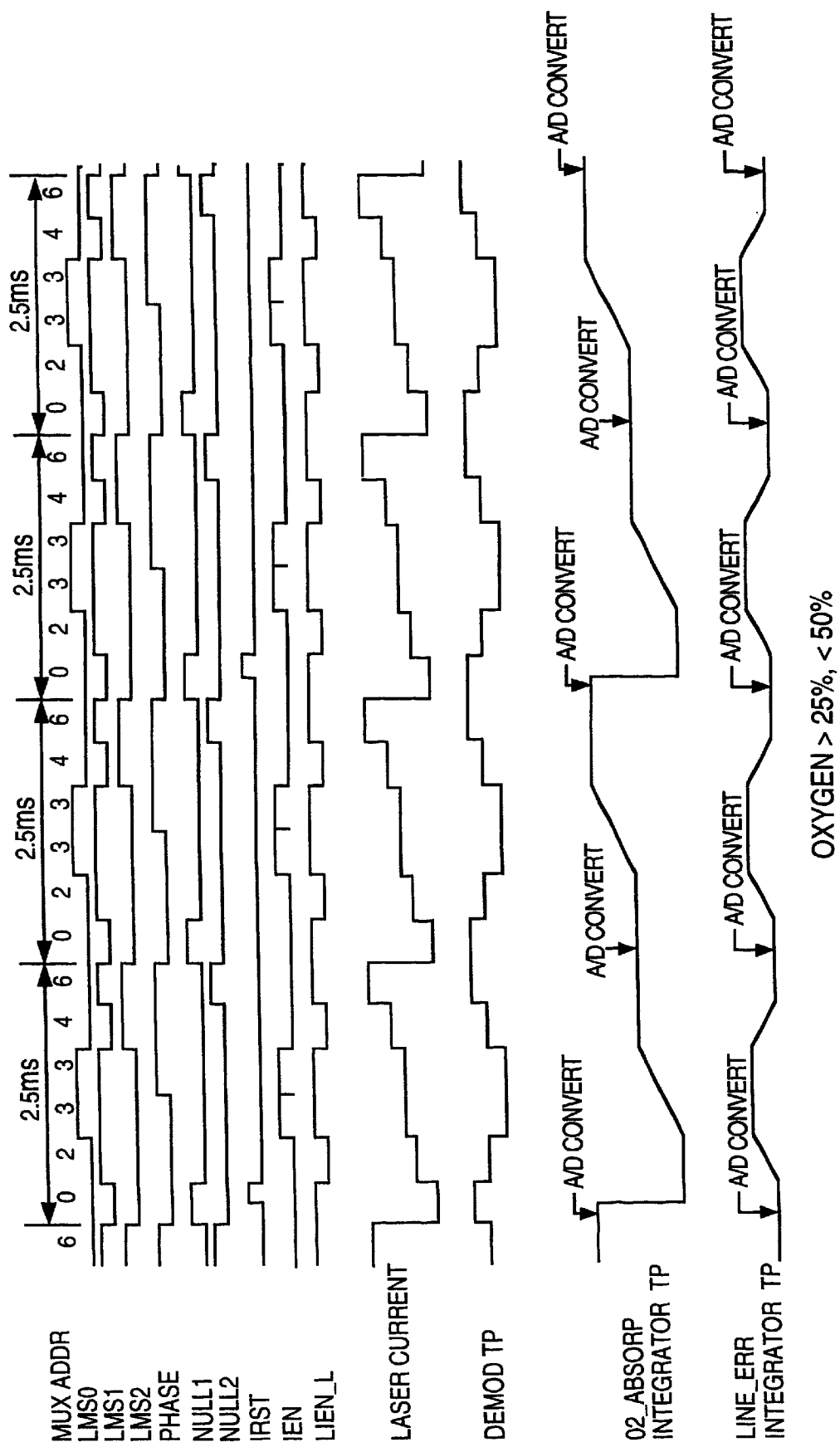
Figure 6B:
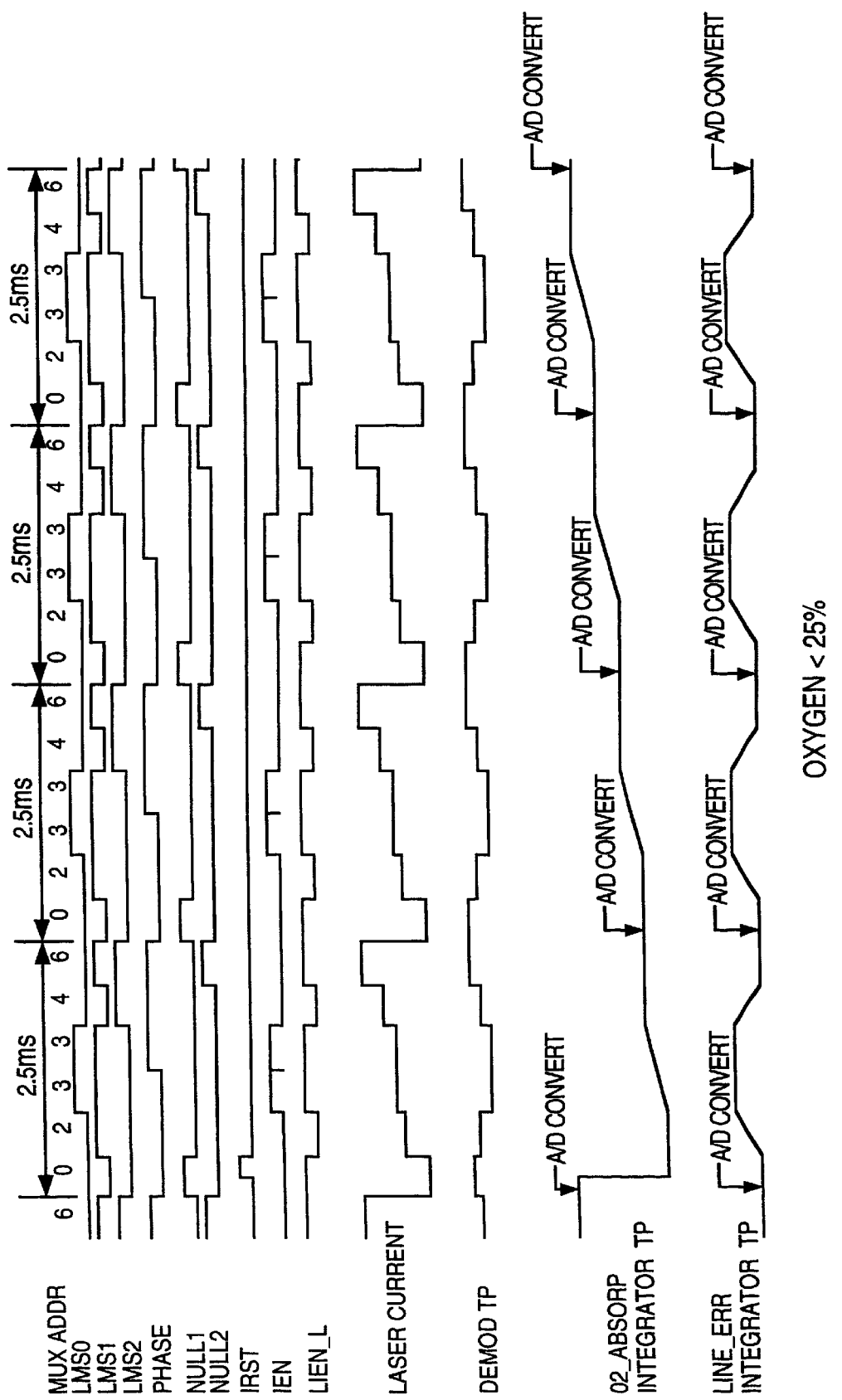
Figure 7E:
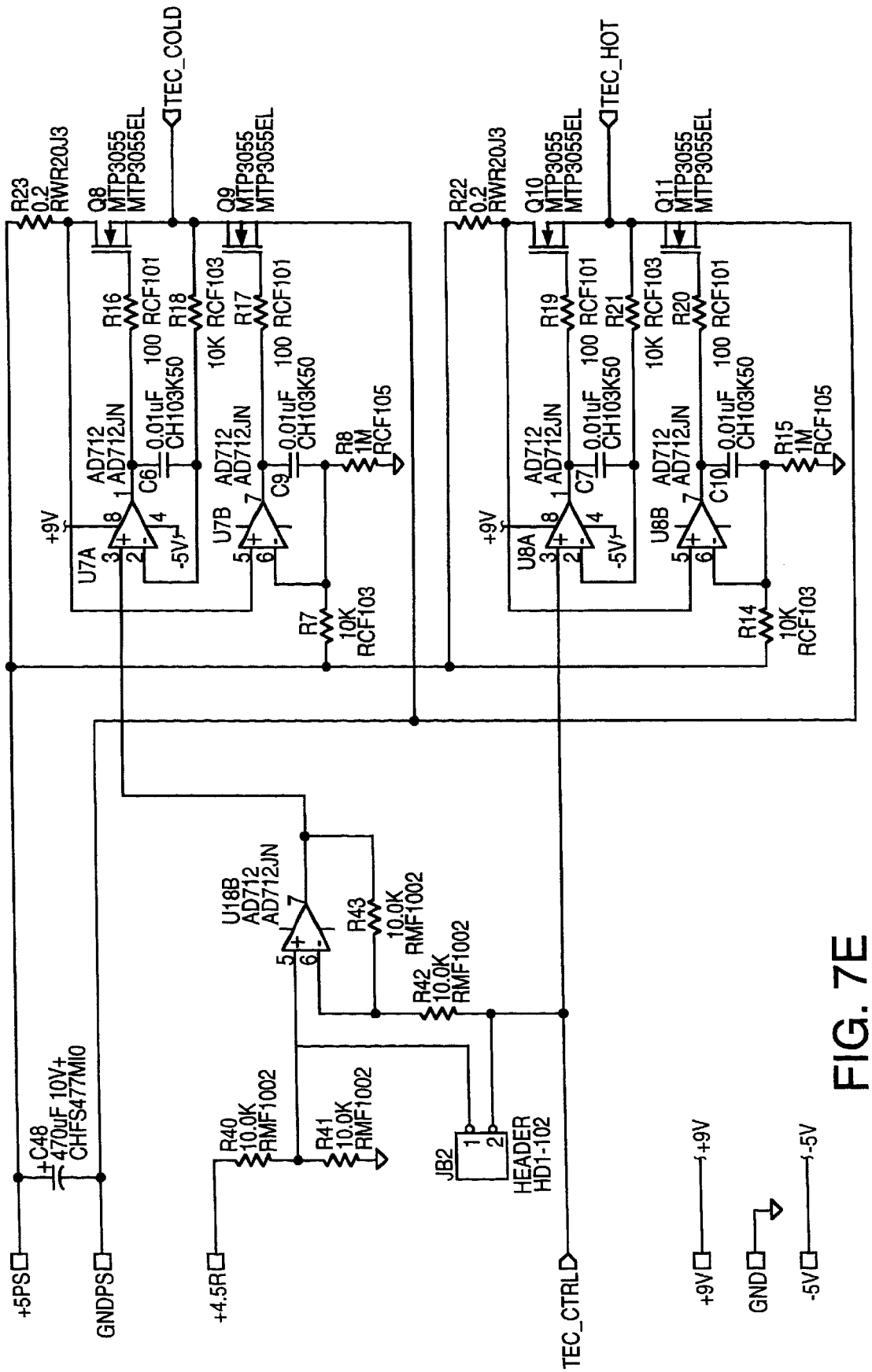
Figure 7F:
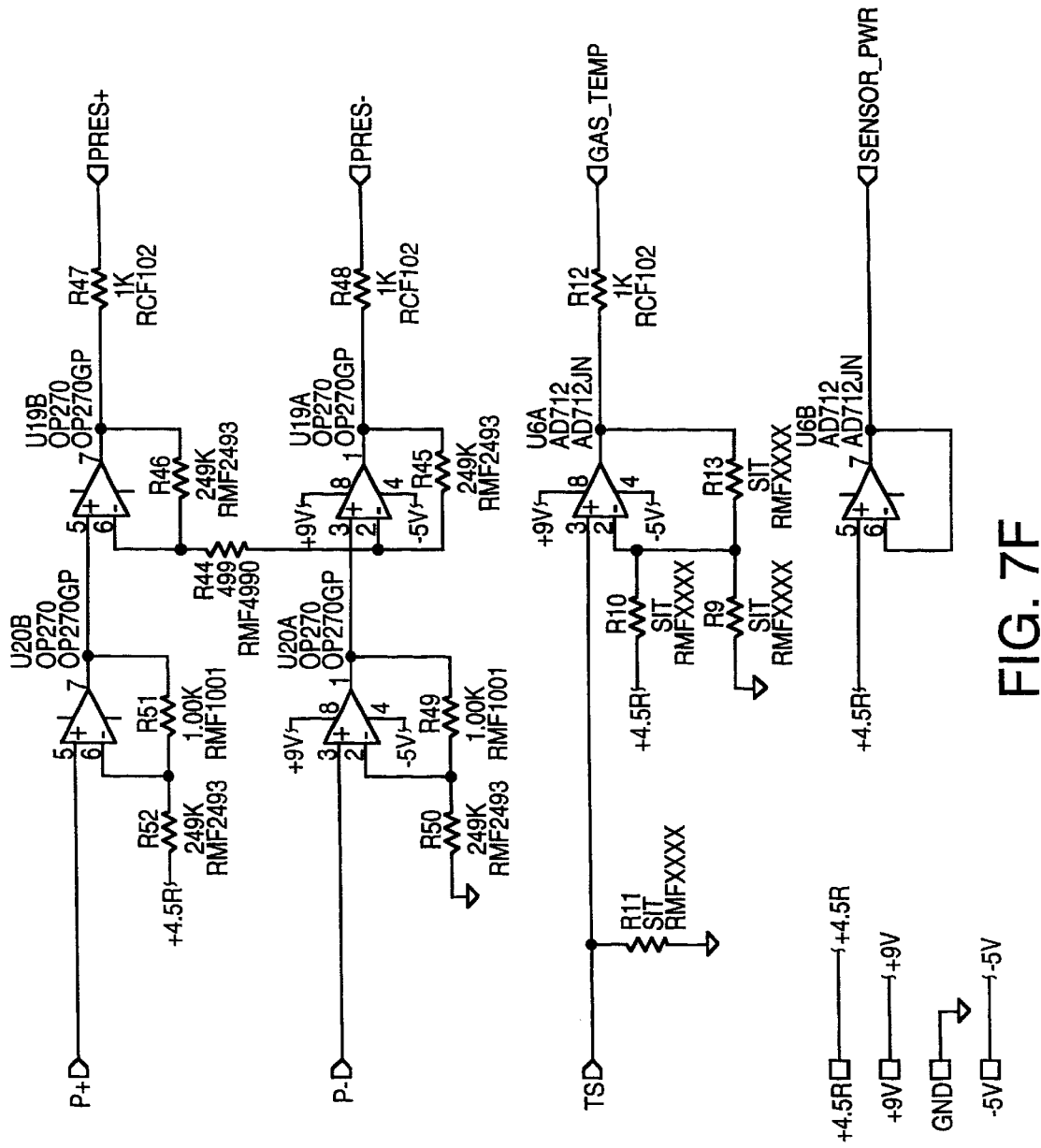
Figure 7G:
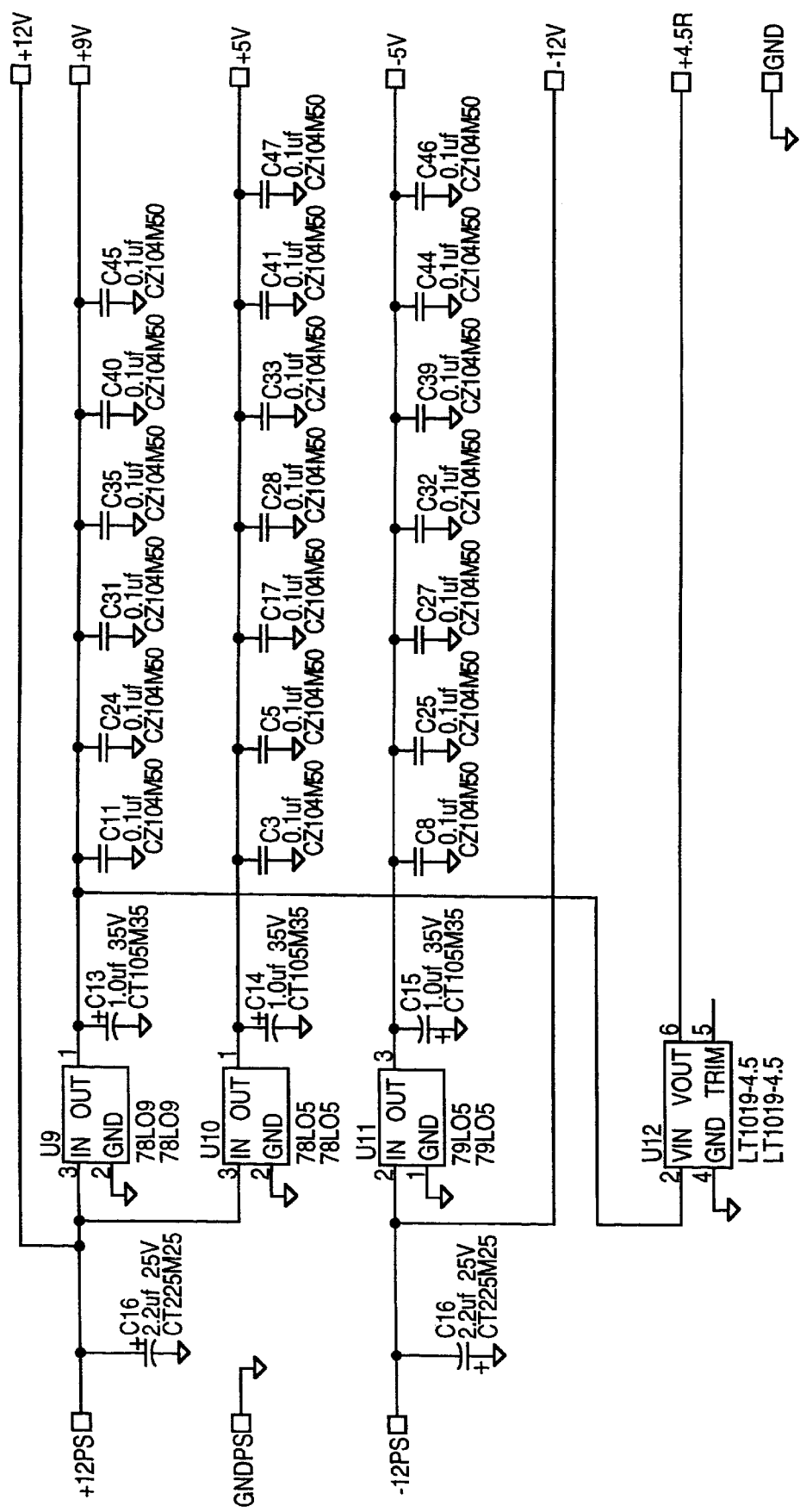

Whereas FIG. 6 illustrates the operation of the oxygen concentration spectroscopy device when the sample cell is filled with a concentration of 50 to 100 percent oxygen, FIG. 6A illustrates the operation of the device with 25 to 50 percent oxygen, and FIG. 6B illustrates the operation of the device with less than 25 percent oxygen. After the voltage DEMOD TP indicative of oxygen absorption in the sample cell is integrated over one peak interval as illustrated in the waveform O2_ABSORP, the value of the integrated voltage is converted into a digital value by the analog-to-digital converter of the microcontroller. If the measured magnitude of this voltage is within the upper 50 percent of the values representable by the digital value output by the analog-to-digital converter, then the digital value is used as the $O_2$ measurement, the integrator is reset by the signal IRST, and the process is repeated as illustrated in FIG. 6. This $O_2$ measurement of 100 percent oxygen, for example, may have a resolution of one part in 256 parts if an eight-bit analog-to-digital converter is used.

If, on the other hand, the measured magnitude of the integrated voltage as determined by the analog-to-digital converter is within the lower 50 percent of the values representable by the digital value, then the IRST signal does not reset the integrator. As a consequence, the integration of the subsequent peak interval increases the integrated voltage still further. At the end of the second period of integration, the analog-to-digital converter again converts the integrated voltage and the microcontroller tests this digital value. This process of increasing the integrated voltage and testing the result continues until another period of integration would either exceed the maximum value representable by the digital value or would cause the integrator to rail. In this case, the digital value generated by the last analog-to-digital conversion represents the sum of n absorbance measurements, where n is the number of intervals over which the integrated voltage was developed. The $O_2$ absorbance measurement is therefore determined to be the digital value divided by n. The integrator is then reset by the signal IRST and the process is repeated. In the case of FIG. 6B where four successive peak intervals of approximately 25 percent oxygen are integrated with an eight-bit analog-to-digital converter, the $O_2$ measurement will still have a resolution approximately equal to one part in 256 parts. If 25 percent oxygen were detected without accumulating an integrated value over four multiple periods, the resolution would be one part out of 64. This autoranging technique therefore results in high resolution concentration measurements through the full range of 0 percent oxygen to 100 percent concentration.

In some embodiments, dual slope integration may be used. After an integrator changes a voltage from a starting voltage to an integrated voltage indicative of sample cell absorption, the integrator is made to integrate in opposite direction at a known rate until the starting voltage is again achieved. The monitor photodiode fractional current, for example, may be supplied to an integrator in order to drive the output of the integrator back to a starting voltage of zero volts and a timer input on the microprocessor may be used to determine the amount of time required to reachieve the starting voltage. This technique achieves improved $O_2$ measurement resolution on the order of one part out of 5,000 to 10,000 parts.

FIGS. 7A–7G comprise a more detailed schematic diagram of the oxygen detector described above in connection with the simplified schematic of FIG. 5 and the timing diagram of FIG. 6. Like reference numerals and like signal names reference like circuit elements and like signals in FIGS. 5 and 7A–7G. Potentiometer VR1 adjusts reference level gain Potentiometer VR1 is adjusted by placing 100 percent oxygen into the sample cell and adjusting VR1 until the output of the analog-to-digital conversion is close to full scale.

The current supplied to the thermoelectric coolers in thermal contact with the laser diode housing is controlled by the microcontroller U3 from the pulsewidth modulated output pin 28. The microcontroller U3 controls the pulse width of the signal on pin 28 such that the low pass filtered output on signal line TEC_CTRL in FIG. 7C has a DC magnitude suitable to cause the thermoelectric cooler drivers of FIG. 7E to output the appropriate amount of current. The terminal of each thermoelectric cooler which is to be relatively cold is connected to the terminal TEC_COLD whereas the terminal of each thermoelectric cooler which is to be relatively hot is connected to the terminal TEC_HOT.

Because the pressure of the gas in the sample cell has an effect on the absorption measurement, the pressure of the gas exiting the sample cell is measured by a pressure transducer and is read by microcontroller U3. The spectral absorption linewidths of oxygen, for example, may spread when oxygen pressure in increased. FIG. 7A illustrates a pressure sensor PSI having outputs P+ and P−. After processing by the pressure interface circuitry illustrated in FIG. 7F into analog signals PRES+ and PRES−, the microcontroller U3 illustrated in FIG. 7B senses these analog voltages PRES+ and PRES− on analog-to-digital input pins 48 and 50, respectively.

Not only does pressure have an effect on the absorption measurement, but the temperature of the sample gas also has an effect on the absorption measurement. FIG. 7A illustrates a thermistor TS1 through which a signal is generated indicative of the temperature of the gas inside the sample cell. The analog signal TS output from the thermistor is isolated into analog signal GAS_TEMP by the circuitry of FIG. 7F and is sensed by the microcontroller U3 of FIG. 7B on analog-to-digital input pin 46.

Figure 8:
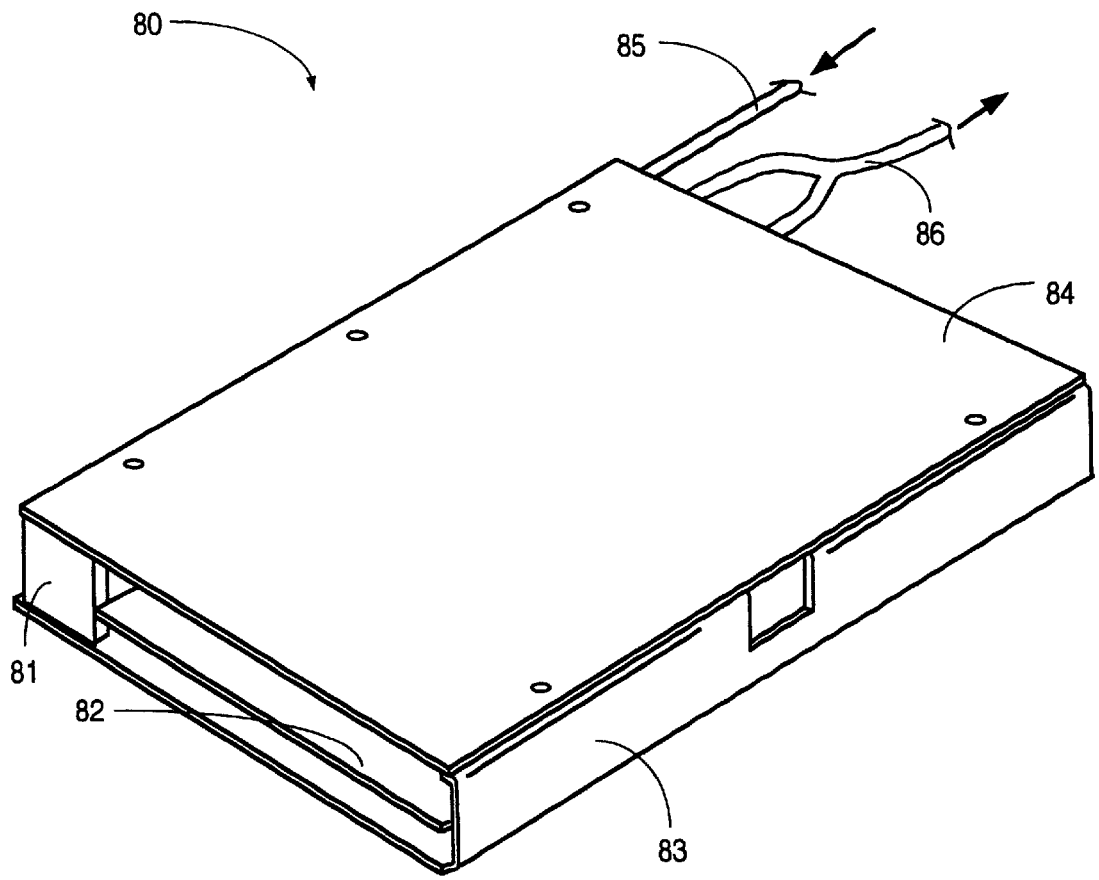
FIGS. 8–12 are views of a gas spectroscopy device in accordance with one embodiment of the present invention.

FIG. 8 is perspective view of a gas spectroscopy device 80 in accordance with one embodiment of the present invention. The gas spectroscopy device comprises a sample cell/line locking cell assembly 81 and a populated printed circuit 82 disposed within a thermally conductive enclosure comprising metal base member 83 and metal cover member 84. An input tube 85 is shown in FIG. 8 through which gas is input into the sample cell/line locking cell assembly 81. An output tube 86 is shown in FIG. 8 through which gas from the sample cell/line locking cell assembly is exhausted.

Figure 9:
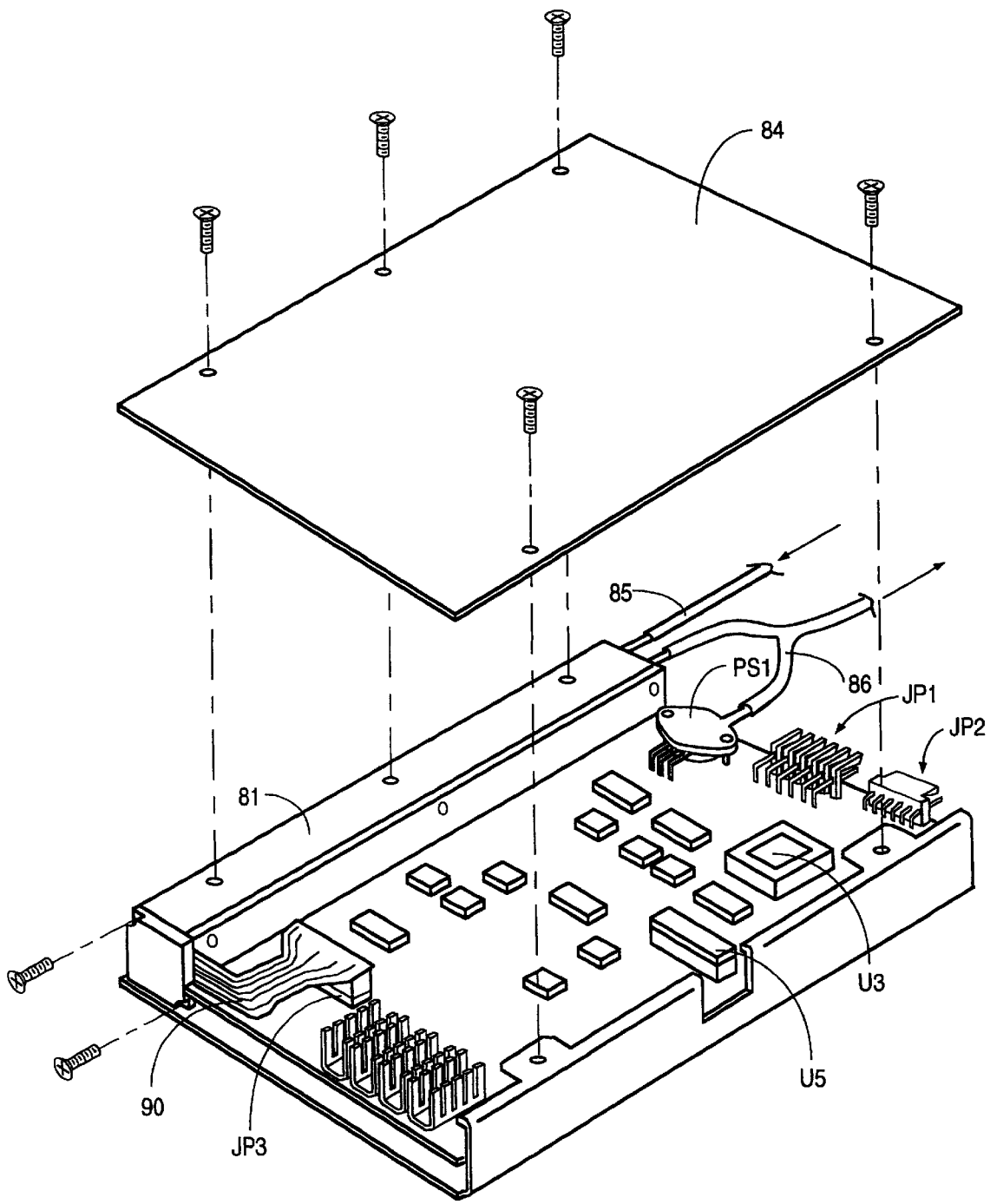

FIG. 9 is an exploded perspective view of the gas spectroscopy device 80 of FIG. 8 with the cover 84 removed. Pressure sensor PS1 is shown connected to the output tube 86 so that pressure sensor PS1 can detect the pressure of the gas flowing out of the sample cell/line locking assembly. A power connector JP1 and a serial interface connector JP2 are provided at one end of the printed circuit board. Various of the circuit elements of the detailed schematic of FIGS. 7A–7E are disposed on the printed circuit board including the 68HC711E9FN microcontroller U3 and the EP610 programmable integrated circuit U5 which implements the sequencer. The circuitry on the printed circuit board controls and senses the sample cell/line locking cell assembly 81 via a flexible circuit 90 which connects to jumper JP3 on the printed circuit board.

Figure 10:
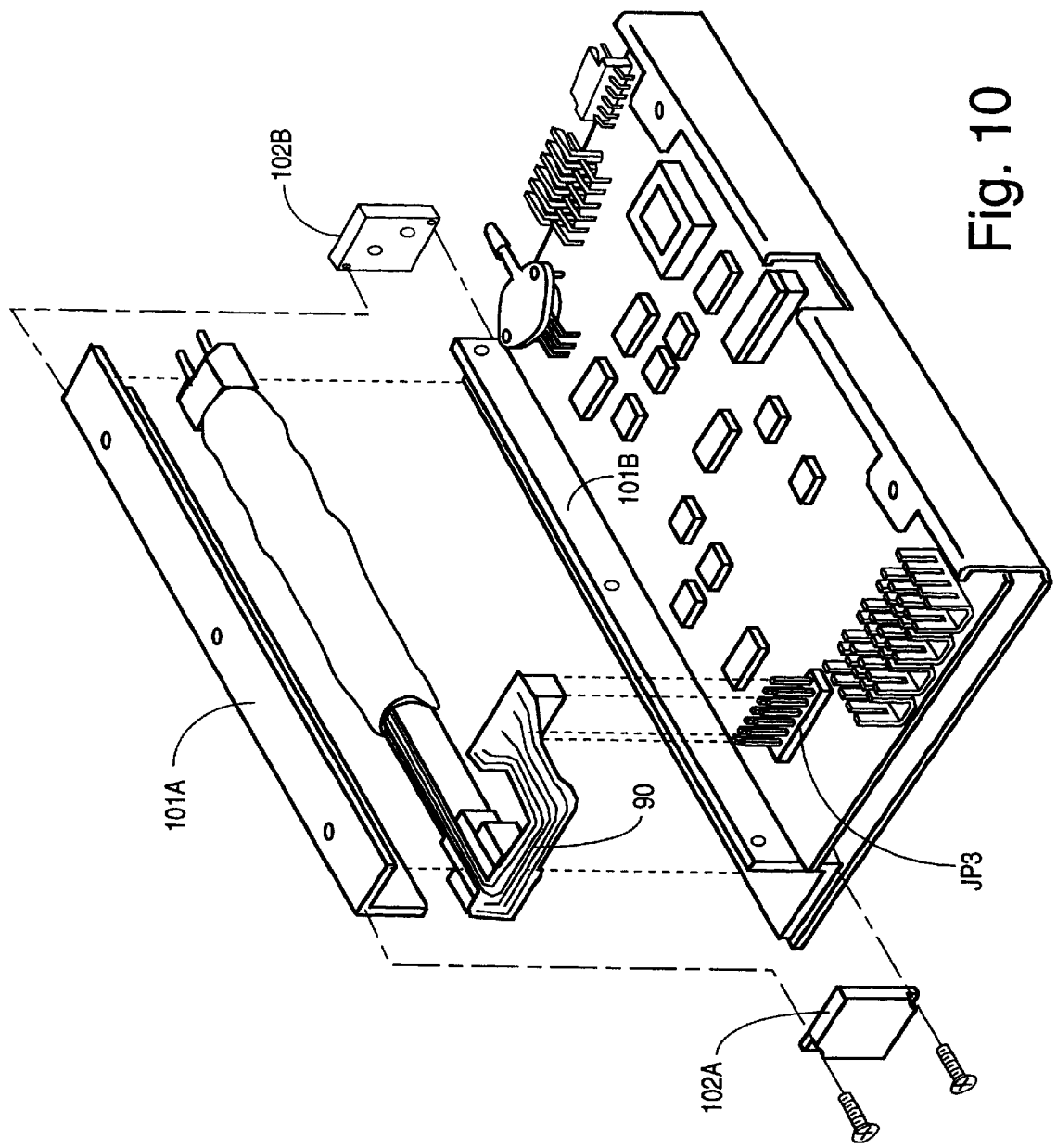
Figure 11:
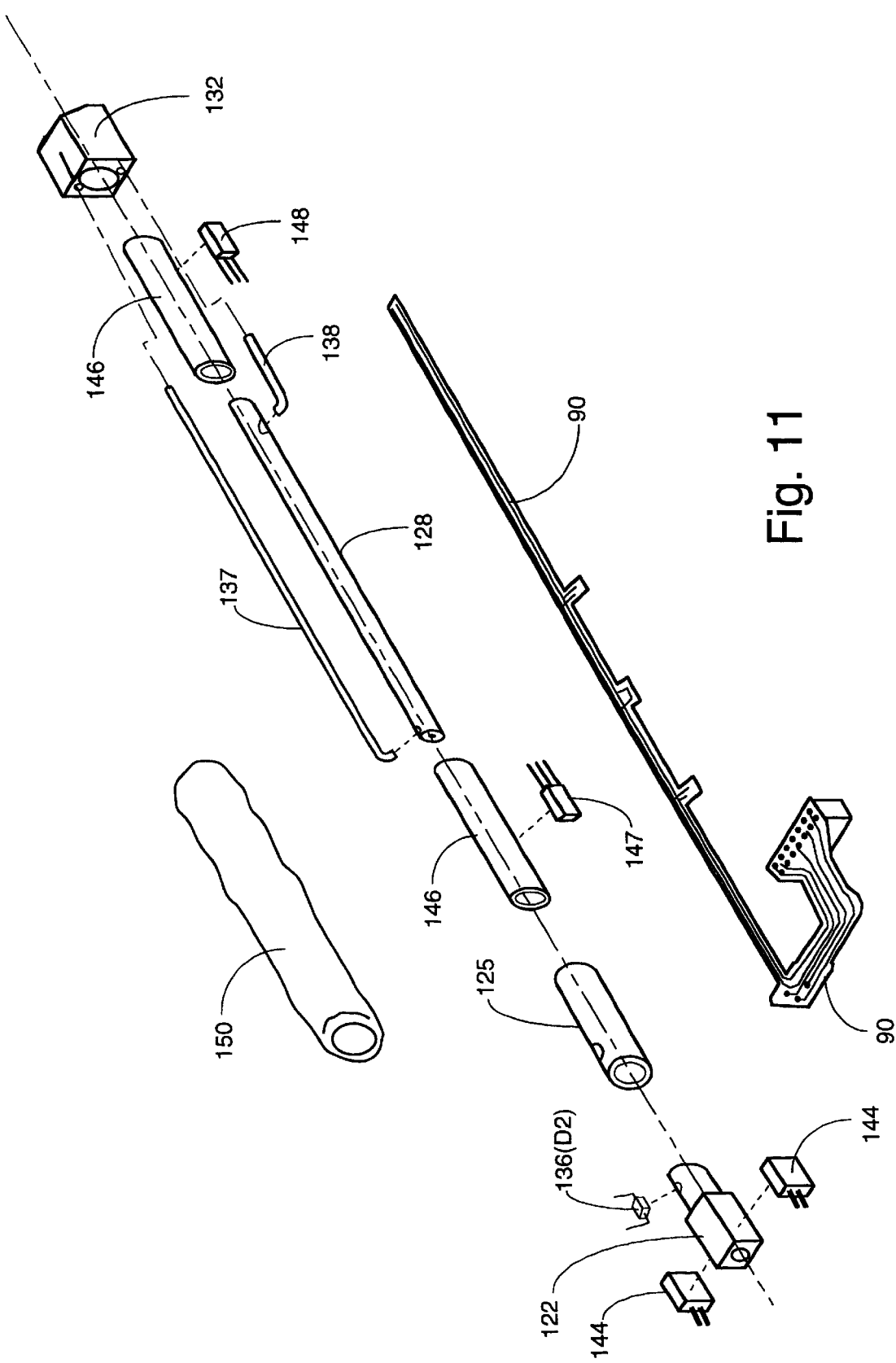

FIG. 10 is an exploded perspective view of the gas spectroscopy device of FIG. 9 with the sample cell/line locking cell assembly exploded so that heat sink support members 101A and 101B and end members 102A and 102B are removed revealing the internal components of the sample cell/line locking cell assembly. FIG. 11 is an exploded view of the internal components of the sample cell/line locking cell assembly.

Figure 12:
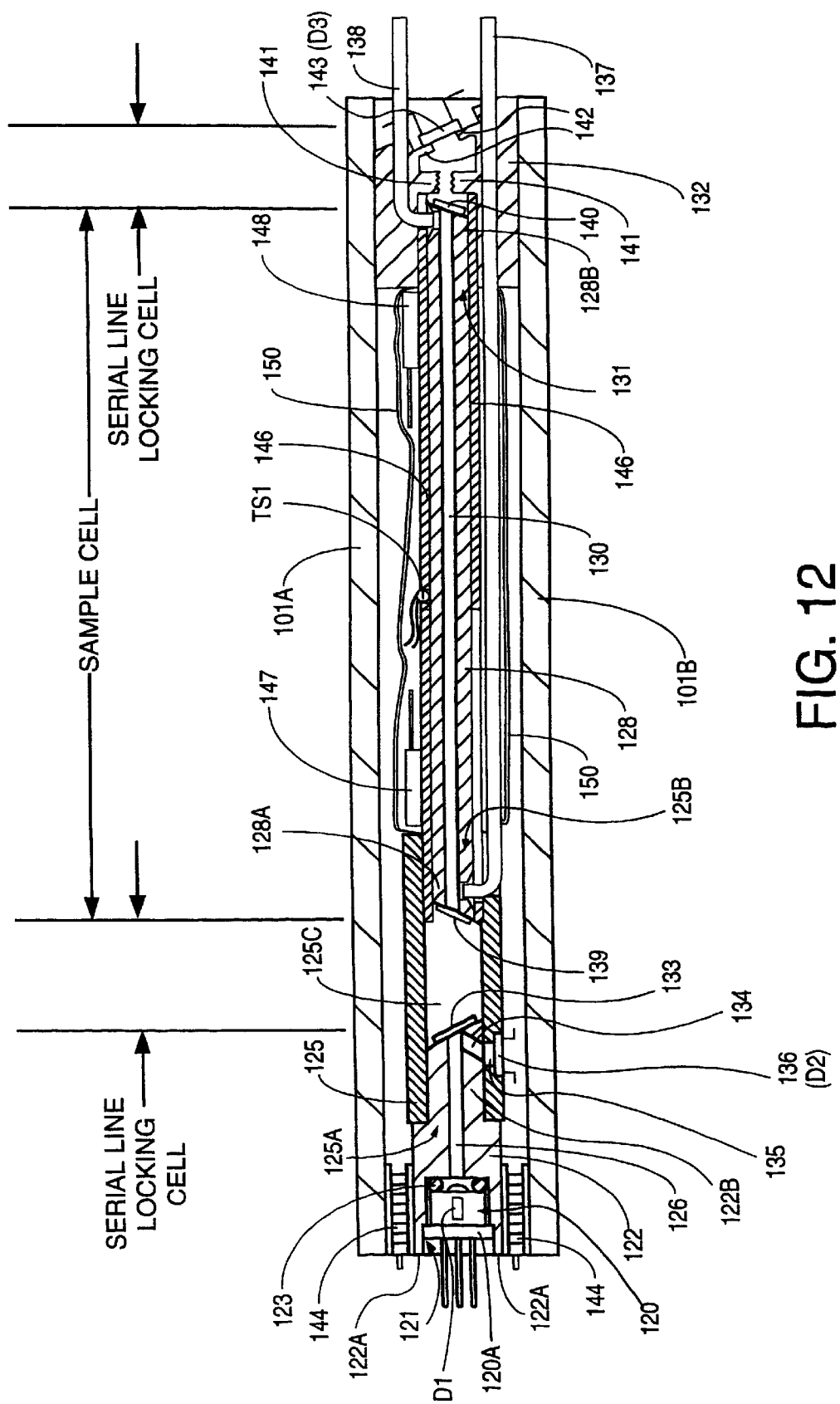

FIG. 12 is top down cross-sectional view of the components of the sample cell/line locking cell assembly. A laser diode/lens assembly 120 comprising a lens fixed by an adhesive to a laser diode housing has a base portion 120A having a planar ledge reference surface. This planar reference surface is pressure fitted into cylindrical mounting opening 121 in first end 122A of laser mounting member 122 until the laser diode housing compresses rubber o-ring 123 and a ledge reference surface of base portion 120A is pressed against and therefore spatially referenced to an inside ledge reference surface of laser mounting opening 121 of laser mounting member 122.

A second end 122B of laser mounting member 122 is disposed in first end 125A of joining tube member 125. A beam splitter 133 is disposed on the end 122B of laser mounting member 122 so that a portion of a laser radiation beam emitted from laser/diode lens assembly 120 is reflected through monitor hole 134 in the laser mounting member 122, through monitor hole 135 in joining tube member 125, and to monitor photodetector 136 (D2) which is fixed to the joining tube member 125.

A first end 128A of a sample cell tube member 128 is disposed in second end 125B of joining tube member 125 so that axial hole 130 in sample cell tube member 128 is aligned with axial hole 126 in the laser mounting member 122. Sample cell tube member 128 may, for example, be made of a plastic material. In the preferred embodiment sample cell tube 128 is fabricated from glass capillary tubing obtained from Schott Glass, PN#31140876 which has a 8.380±0.2 mm outside diameter and a 1.575 ±0.013 mm inside diameter. The small diameter of the axial hole 130 in the sample cell tube member 128 allows measurements of oxygen concentration to be made quickly upon the introduction of only a small volume of sample gas into the axial hole 130.

A second end 128B of sample cell tube member 128 is disposed in receiving opening 131 of a photodetector holding member 132. A first window 139 is disposed on end 128A of sample cell tube member 128 and a second window 140 is disposed on end 128B of sample cell tube member 128 in order to seal axial hole 130 of sample cell tube member 128 to create a sample cell. An end of a metal input tube 137 is disposed in a hole in sample cell tube member 130 and an end of a metal output tube 138 is disposed in another hole in sample cell tube member 130 so that sample gas can flow into the sample cell through input metal tube 137, flow through axial hole 130, and can be exhausted from the sample cell through output metal tube 138. The windows 139 and 140 as well as airway tubes 137 and 138 are epoxied to the sample tube to form an airtight sample cell.

In one embodiment, photodetector holding member 132 comprises a tube portion 141 as well as a radiation trap portion 142. A signal photodetector 143 (D3) is fixed to photodetector holding member 132 in such a position that a beam of laser radiation emitted from laser diode/lens assembly 120 passes through axial holes 126, 125C and 130, passes through tube portion 141, passes through radiation trap portion 142, and is incident on signal photodetector 143 (D3). The inside surface of tube portion 141 has a rough surface to attenuate laser radiation which otherwise might pass back through tube volume 141 after being reflected off signal photodetector 143 (D3) and then being reflected off the inside surface wall of tube portion 141. The radiation absorbing rough inside surface of the tube portion 141 tends to absorb and/or to reflect laser radiation in such a manner that little radiation subsequently passes back into the axial hole 130. Radiation trap portion 142 is provided to additionally attenuate laser radiation which is reflected off the signal photodetector 143 (D3) but which does not reflect with an appropriate angle to pass directly into the tube portion 141. The structure of the radiation trap portion serves to cause much of this laser radiation to reflect off multiple radiation absorbing inside surfaces of the radiation trap portion 142 before this laser radiation obtains a appropriate direction to pass into tube portion 141. The radiation trap portion therefore serves to attenuate laser radiation before it enters tube portion 141.

Not only does the structure of FIG. 12 have a sample cell, but the structure of FIG. 12 has a serial line locking cell disposed in series with the sample cell. The line locking cell contains a reference gas which is used to lock the frequency of the laser radiation emitted from the laser diode/lens assembly 120 to a spectral line of the reference gas in the serial line locking cell. Whereas other gas spectroscopy devices use the sample gas in the sample cell to lock onto a spectral line and therefore cannot measure low sample gas oxygen concentrations in the range of approximately 0–5%, the device of FIG. 12 locks onto a reference gas known to be in the serial line locking cell and therefore can be locked to detect sample gas concentrations in the sample cell down to approximately 0%. Dual beam gas spectroscopy devices utilize a sample gas optical path and in addition a reference gas optical path to allow the laser radiation to lock onto an absorption line. By placing both the reference gas and the sample gas in the same path of a laser beam not requiring a separate reference gas optical path, the expense of the spectroscopy device is reduced and the resulting spectroscopy device can be made more compact.

In the embodiment illustrated in FIG. 12, the reference gas to which the laser radiation is locked is present in the volume between beam splitter 133 and window 139 of the sample cell tube member 88. The reference gas is also present in volume enclosed by the tube portion 141 and volume enclosed by the radiation trap portion 142. The specific serial line locking cell illustrated is therefore comprised of two parts, one part being present on one side of the sample cell, the other being present on the other side of the sample cell.

In some embodiments, the serial line locking cell is open to ambient air. In other embodiments, the serial line locking cell is supplied with a reference gas with a constituent combination other than ambient air. In some embodiments, the serial line locking cell is sealed with a reference gas which contains relatively little water vapor and which has a known gas constituent concentration. In some embodiments, the pressure and/or temperature of the reference gas may be controlled. In some embodiments, the sample gas is not contained in a sealed sample cell but rather is a volume of sample gas through which the beam of laser radiation passes.

To prevent laser radiation that reflects off the beam splitter 133, the first and second windows 139 and 140, and the photodetectors 143 (D3) and 136 (D2) from being reflected straight back into the laser diode D1, the beam splitter 133, the first and second windows 139 and 140, and the photodetectors 143 (D3) and 136 (D2) are each positioned at an angle with respect to the axis of the beam of laser radiation which passes from the laser diode/lens assembly 120 to the signal photodetector 143 (D3) and to monitor photodetector 136 (D2). Reflections off these structures therefore tend to be attenuated. The first and second windows and the photodetectors may also be coated with a low scatter coating such as an antireflection coating to further reduce unwanted reflections.

The beam of laser radiation emitted from laser diode/lens assembly 120 need not be highly collimated because the measurement is not an optical phase sensitive measurement. Most of the non-collimated radiation which enters the serial line locking cell and the sample cell is in some embodiments, reflected down axial holes 126 and 130 at a grazing incidence and is received by signal photodetector 143 (D3). In the embodiment shown in FIG. 12, signal photodetector 143 (D3) is located approximately 6.5 inches from the lens of the laser diode/lens assembly 120. In the embodiment of FIG. 12, the lens of the laser diode/lens assembly is positioned in the X-Y plane so that the central axis of the beam which is output by the laser diode is within a tolerance of 0 to 0.3 degrees to an axis, where the axis is normal with respect to the plane of the ledge reference surface of the laser diode/lens assembly 120.

The laser diode/lens assembly 120 generates a semi-collimated beam of laser radiation which passes through the reference gas in the serial line locking cell, through the sample cell, and to signal photodetector 136 (D2). Photodetectors 143 (D3) and 136 (D2) are used to differentially determine the amount of absorption of laser radiation which occurs in the sample cell as described above. A pair of thermoelectric coolers 144 are provided, one of which is disposed between support member 101A and laser mounting member 122, the other of which is disposed between support member 101B and laser mounting member 122. The two thermally conductive support members 101A and 101B function as a heat sink together with the thermally conductive base and cover members 83 and 84 (see FIG. 8). In the embodiment of FIGS. 12, support members 101A and 101B each have an angled shape and are joined by screws. Laser mounting member 122 is made of thermally conductive material such as a metal so that the thermoelectric coolers 144 can efficiently and accurately cool the laser diode D1 inside the laser mounting member 122. Heat from the laser diode/lens assembly base portion 120A is removed causing heat to be removed from the diode D1 inside the laser diode/lens assembly 120 via the thermoelectric coolers 144 and is radiated away via the thermally conductive support members 101A and 101B. Support members 101A and 101B also function to hold the photodetector holding member 132 in a stable position with respect to laser mounting member 122 so that the laser diode/lens assembly, the serial line locking cell, the sample cell, and photodetectors remain in proper alignment. Thermoelectric coolers are used as a coarse method of wavelength tuning of the laser diode via changing the temperature of the laser diode housing and thereby the laser diode chip. Fine temperature adjustment of diode temperature is performed by controlling the magnitude of current supplied to the laser diode as described above.

Because one application of the gas spectrometry device of FIG. 12 involves the analysis of human breath and more specifically involves determining the oxygen concentration in human breath, the sample cell is heated to avoid water vapor in human breath from condensing on windows 139 and 140 and on the inside surface of axial tube 130. A thermally conductive sheath 146 is therefore placed around sample cell tube member 128 and heater transistors 147 and 148 are placed in thermal contact with the sheath so that the sheath 146 can be heated by the heater transistors to a controlled temperature based on a temperature detected by thermistor TS1. A covering 150, which in the preferred embodiment is a heat shrink covering, is used to maintain the sample cell tube member 128 in the same thermal environment as the temperature controlled sheath and the input tube 137. Joining tube member 125 is therefore made of a thermally nonconductive material such as plastic or the like so that the temperature of the sample cell can be maintained at a temperature which is different from the temperature of the laser mounting member 122 and laser diode. With this construction, human breath passing into the sample cell at a flow rate of 150 ml/minute through an input tube 137 having a diameter of 1/16 inches is heated during its passage through the heated input tube 137 to a temperature adequately close to the temperature of the windows 139 and 140 such that water vapor in human breath does not condense inside the sample cell. This also preheats the sample gas to a known temperature as determined by the sample cell heater circuitry.

Figure 13A:
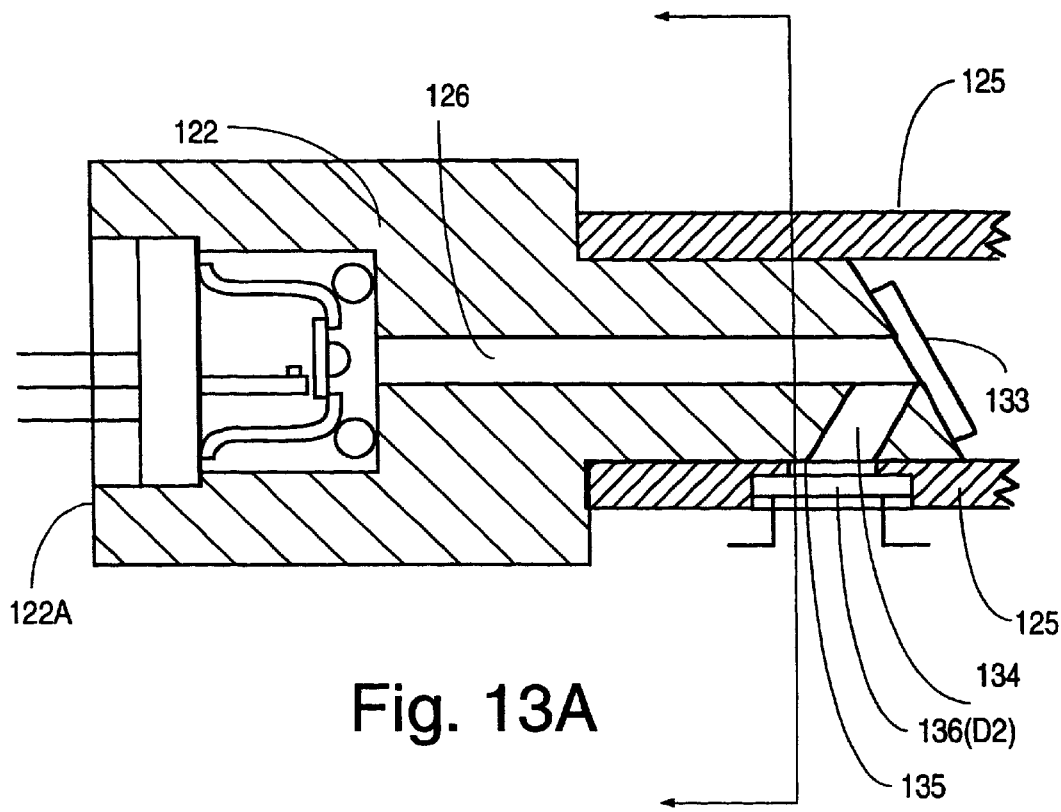
FIGS. 13A and 13B are detailed cross-sectional views of the laser mounting member of the embodiment of FIGS. 8–12.
Figure 13B:
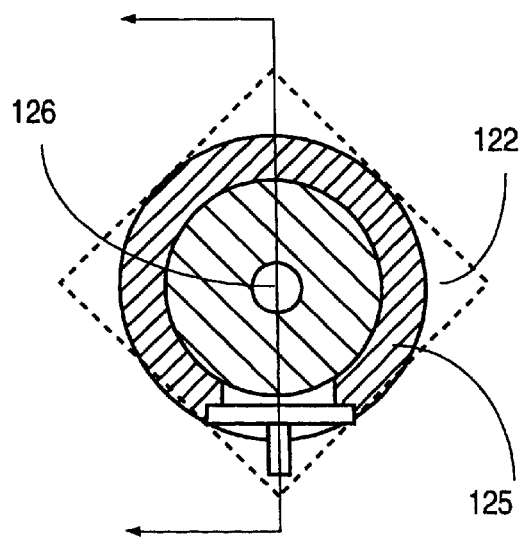
Figure 14:
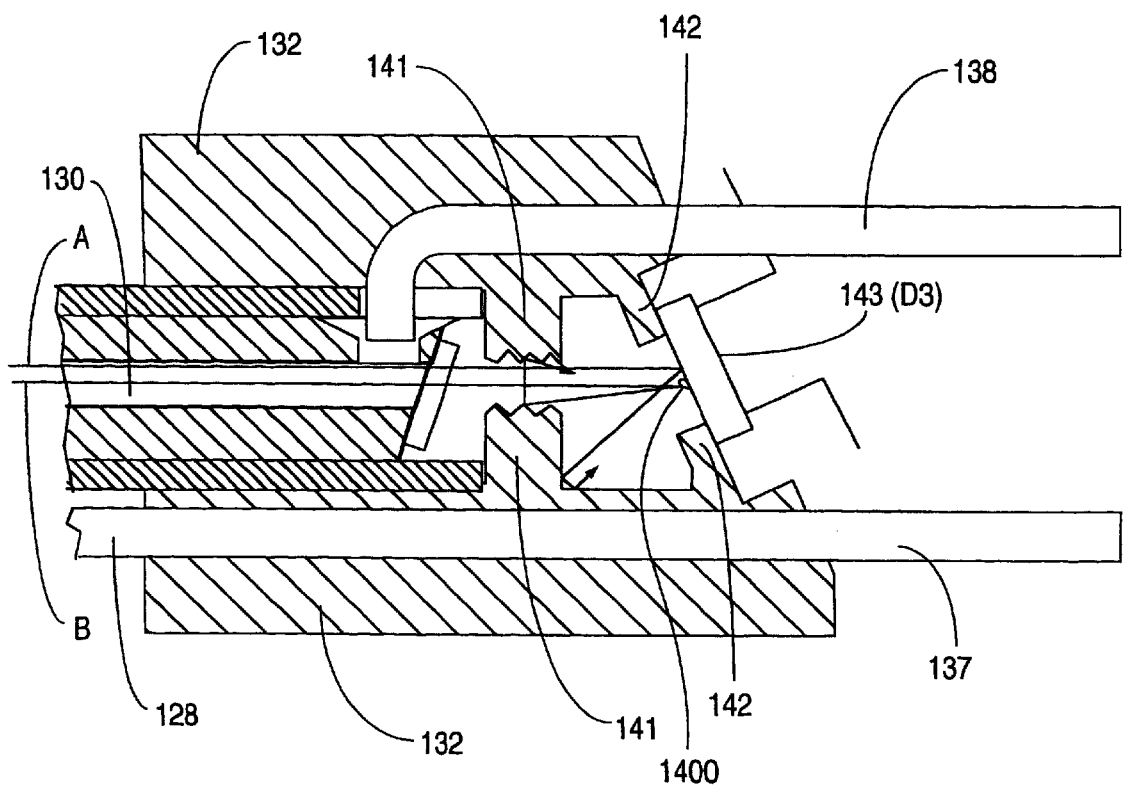
FIG. 14 is a detailed cross-sectional view of the photodetector holding member of the embodiment of FIGS. 8–12.

FIGS. 13A and 13B are more detailed cross-sectional views of the laser mounting member 122. FIG. 14 is a more detailed cross-sectional view of the photodetector holding member 132. A laser radiation ray A is illustrated reflecting off angled signal photodetector 143 (D3) such that ray A later reflects off the inside surface of radiation trap portion 142 rather than being reflected straight back through the hole in tube portion 141 and into the axial hole 130 of the sample cell. In the event that laser radiation scatters off the angled signal photodetector at another angle, then the laser radiation may be scattered back to be incident on the inside surface of the hole in tube portion 141. A laser radiation ray B is illustrated scattering after hitting a dust particle 1400 disposed on signal photodetector 143 (D3). The rough inside surface of the hole in tube portion 141 prevents ray B from simply being reflected off the inside surface of the hole and back into the sample cell. In some embodiments, a tube portion is provided but no trap portion is provided.

Radiation which is reflected back to the laser diode may interfere with the controlled single-mode operation of the laser diode. The laser diode is a gain medium for radiation of the frequency of the laser radiation. Radiation which is scattered off surfaces in the spectroscopy device such that radiation passes back to the laser diode will be amplified by the laser diode. Accordingly, in order to preserve the single-mode operation of the laser diode, it is desirable to reduce radiation scattered back to the laser diode.

Figure 15:
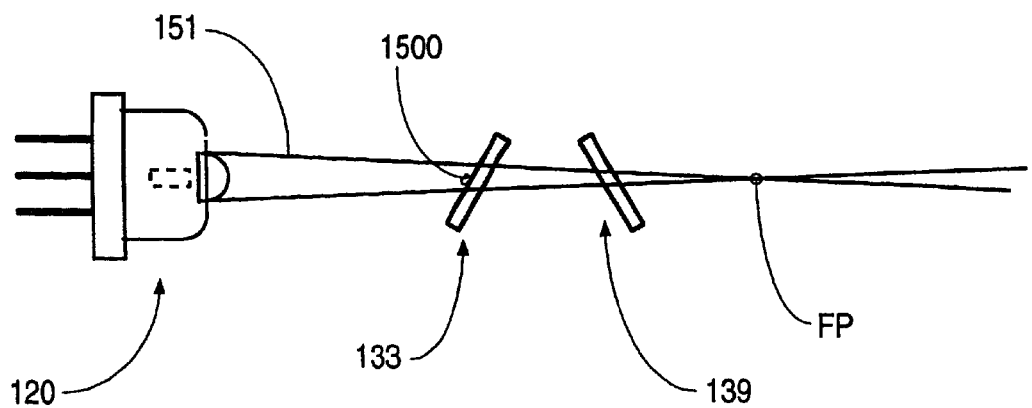
FIG. 15 is an illustration of a structure and method for reducing the effect of unwanted reflections in a spectroscopy device in accordance with the present invention.

FIG. 15 illustrates a structure which results in a reduction of radiation being scattered off dust particle 1500 and back into the laser diode of the laser diode/lens assembly 120. Rather than focussing the beam 151 of laser radiation emitted from the laser diode/lens assembly 120 either on or near a surface such as a surface of beam splitter 133 or a surface of window 139, the beam 151 is focussed at a point FP beyond these surfaces within the sample cell. By reducing the power density of laser radiation incident upon the surfaces where scatter may occur but through which the beam of laser radiation must nevertheless pass, the magnitude of laser radiation which scatters off those surfaces is reduced. In order to reduce unwanted reflections, it is generally desirable to have large beam splitter and window area surfaces with the beam 151 passing through large areas of the beam splitter and window surfaces. In order to achieve fast response time in the spectroscopy measurement with the spectroscopy device, however, small diameter sample cell windows are desirable to reduce the volume of gas in the sample cell.

Figure 16:
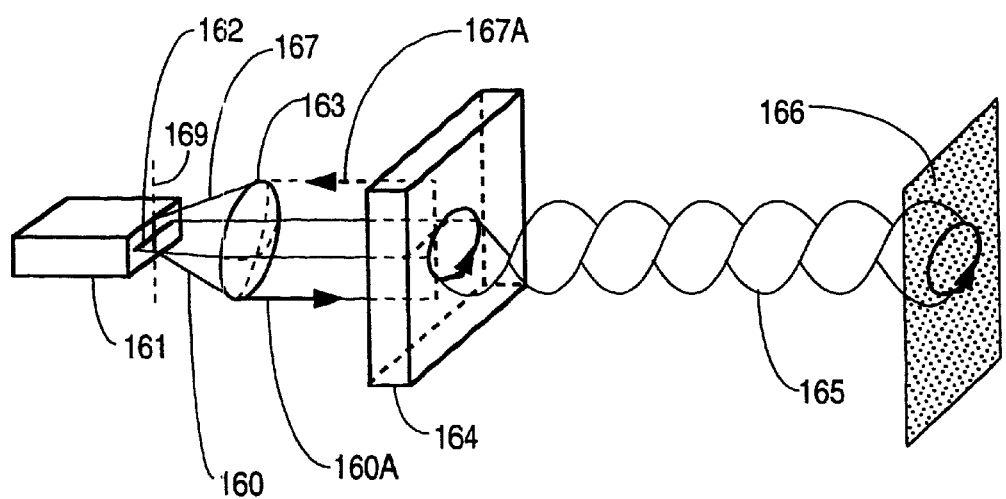
FIG. 16 is an illustration of a structure comprising a quarter wave plate in accordance with the present invention.

FIG. 16 illustrates another structure which results in the reduction of laser radiation being scattered back to the laser diode of a spectroscopy device. Laser radiation 160 emitted from a laser diode 161 is typically emitted from a narrow slit 162 of the laser diode structure so that the laser radiation 160 is linearly polarized in the dimension of the slit. The laser diode housing is not shown in FIG. 16 in order to simplify the illustration. Laser radiation 160 may, for example, be linearly polarized by a factor of 100 to 1. The beam of laser radiation 160 emitted from laser diode 161 is illustrated as being linearly polarized in the horizontal dimension and then being substantially collimated by a spherical lens 163. A quarter wave plate 164, sometimes called an optical retarder, is disposed in the path of the collimated beam 160A of laser radiation. The quarter wave plate 164 serves to convert the linear polarization of the laser radiation into a beam of laser radiation 165 which has a circular polarization. In FIG. 16, this circular polarization is illustrated as being clockwise polarization. Unwanted reflections of this circularly polarized beam of laser radiation, such as reflections off dust particles 166 or specular or diffuse reflective surfaces which happen to be reflected back through the quarter wave plate 164, emerge from the quarter wave plate 164 as a beam 167A of linearly polarized radiation which is polarized in the vertical dimension 169 rather than in the horizontal dimension. As a result, much of the unwanted reflected radiation 167 which passes through the spherical lens 163 and to the laser diode 161 is not introduced into slit 162 in the laser diode because slit 162 is perpendicular to the polarization vector of beam 167 caused by the reflection. Accordingly, laser diode operation is not significantly disrupted. It is to be understood that the features of FIG. 16 are not illustrated to scale. Moreover, although quarter wave plate 164 is illustrated in FIG. 16 as having a rectangular block shape, the quarter wave plate may have any suitable shape.

Figure 17:
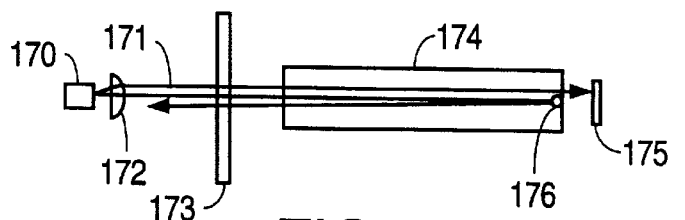
FIG. 17 is an illustration of a structure comprising a neutral density absorber in accordance with the present invention.

FIG. 17 is a block diagram illustration of another structure which reduces the effects of unwanted reflections which otherwise might be introduced back into the laser diode. A laser diode 170 emits a beam of laser radiation, a portion 171 of which passes through a lens 172, passes through a neutral density absorber 173, passes through a sample cell 174, and is then incident on a detector 175. Because the neutral density absorber attenuates the laser radiation which passes through it, the intensity of beam portion 171 supplied to the sample cell is smaller than it would be without the neutral density absorber. The intensity of the laser radiation emitted from the laser diode therefore is increased in order to maintain an intensity at the detector suitable to detect absorbing materials in the sample cell or, as in this preferred embodiment, the detection electronics are more sensitive to maintain signal level. The unwanted reflected laser radiation beam portion which, for example, may reflect off a dust particle such as dust particle 176, must pass back through the neutral density absorber 173 in order to enter the laser diode 170. Such unwanted reflected radiation is therefore attenuated twice as much by the absorber as the desired laser radiation. More importantly, the return reflection into the laser diode is reduced in intensity by the square of the absorption value of the neutral density absorber.

Figure 17A:
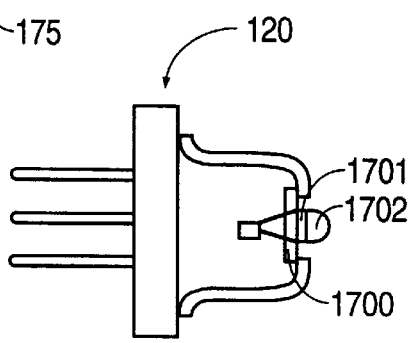
FIG. 17A is a cross-sectional view of a neutral density absorber disposed between a lens and a window of a laser diode/lens assembly.
Figure 17B:
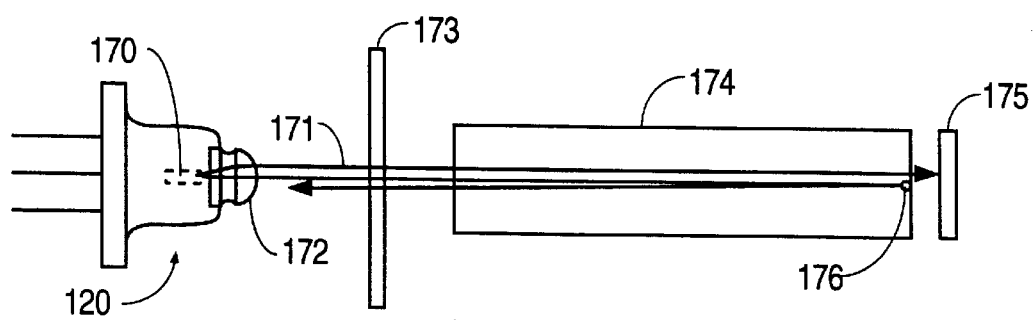
FIG. 17B is a cross-sectional diagram of a structure comprising a neutral density absorber and a lens fixed to a laser diode housing by a volume of adhesive in accordance with the present invention.

FIG. 17A shows a neutral density absorber 1701 disposed between a lens 1702 and a window 1700 of laser diode housing 120. The neutral density absorber 1701 is not disposed in collimated radiation.

The effects of unwanted reflected radiation passing back into the laser diode may be further diminished by using monitor photodiode 136 (D2) and beam splitter 133 to determine the intensity of the radiation emitted from the laser diode. Although a monitor photodiode of the type commonly provided in laser diode housings can be used to indicate the intensity of the beam supplied to a sample cell, such monitor diodes disposed in laser diode housings are generally more sensitive to reflected radiation passing back into the laser diode than is the assembly of the monitor photodiode 136 (D2) and beam splitter 133 which is disposed in the beam path between the laser diode and the sample cell.

Measuring human breath can be done on-airway (in the mainstream) of breathing through a ventilation tube which typically has an inside diameter of 15 millimeters. The advantages of performing spectroscopy on the mainstream compared to performing spectroscopy on a sample removed from the mainstream to a sample cell are several. No pump is needed. No loss of the ventilation mixture occurs which may contain anesthetic gases. No water or aspirate is introduced into a sample cell. There are no chances for air leaks. A spectroscopy device can be brought close to the airway or can be connected to an airway tube by a fiber optic link. Using a single pass across the airway as is common in carbon dioxide airway detectors is not typically suitable for oxygen concentration detectors because oxygen absorption lines are weak.

Figure 18:
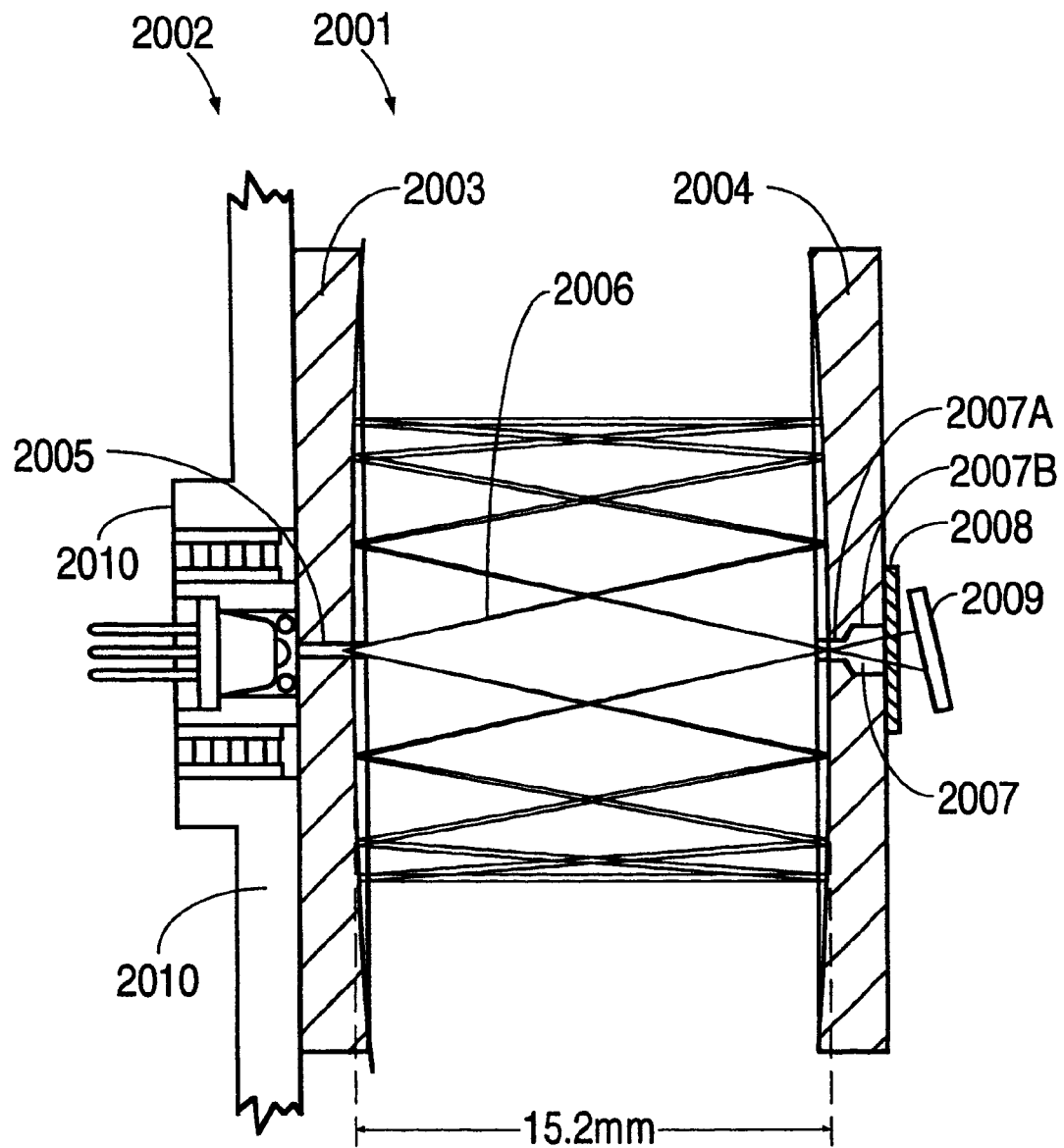
FIG. 18 is a cross-sectional view of an on-airway multiple pass sample cell.

FIG. 18 shows a multiple pass optical cell 2001 connected to a temperature-controlled laser diode assembly 2002. The multiple pass optical cell comprises a first concave mirror 2003 and a second concave mirror 2004. An entrance hole 2005 of a small diameter is disposed in the first concave mirror 2003 so that a beam of radiation 2006, in this case laser radiation, passes through the entrance aperture 2005 and makes multiple passes between the first and second mirrors 2003 and 2004 and then exits the second mirror 2004 through an exit hole 2007. The exit hole 2007 has a relatively small diameter first portion 2007A and a relatively larger diameter second portion 2007B to maximize the reflective area of the second mirror 2004. A window 2008 is provided to retain the sample gas in the volume between the first and second mirrors 2003 and 2004 and is fixed to the outside surface of second mirror 2004. The airway gas sample may, for example, move back and forth between mirrors 2003 and 2004 with inhalation and exhalation in a vertical path. A photodetector 2009 is provided at an angle to detect the radiation 2006 and to determine the radiation absorbed in the sample gas. The laser diode assembly 2002 may, for example, be temperature-controlled by thermal electric coolers as described above in connection with FIG. 12. Similarly, a laser diode/lens assembly may be pressure fitted into a support member 2010 of the laser diode assembly 2002.

Figure 19:
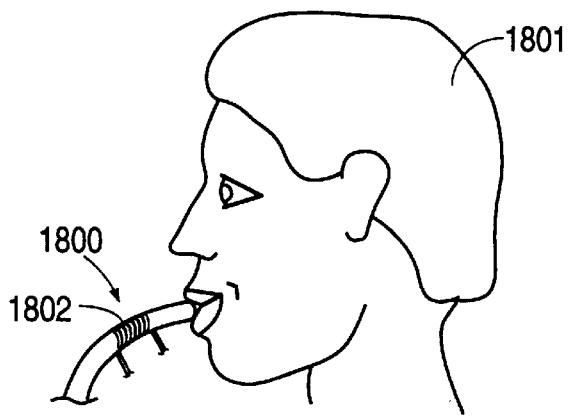
FIGS. 19 and 20 are illustrations of an on-airway evanescent wave structure in accordance with the present invention.

FIG. 19 is an illustration of a structure 1800 usable to detect the concentration of a sample gas such as oxygen in the breath of a patient 1801. Such a structure should be as small and light weight as possible so that it does not unduly interfere with the comfort of the patient. Due to the weak absorption spectral lines of oxygen, a significant optical path length on the order of several inches is generally required so that the sample gas will absorb enough radiation to constitute a reliable measurement. Rather than reflecting laser radiation off multiple reflective surfaces in order to achieve this path length in a compact volume, an optical fiber 1802 is coiled multiple times to achieve a suitable on-airway path length for the detection of oxygen absorption. A evanescent wave of laser radiation which alternately penetrates the fiber optic wall into the surrounding sample gas and returns to the interior of the optical fiber while traveling through the optical fiber of the coil thereby actually passes through the sample gas flowing around optical fiber of the coil.

Figure 20:
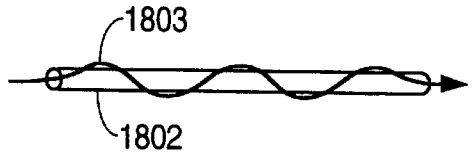

FIG. 20 illustrates an evanescent wave 1803 traveling in a section of optical fiber 1802. The laser radiation 1803 passes outside the fiber and into the gas surrounding the fiber before radiation 1803 turns and reenters the fiber. The optical fiber can be of very small diameter and can be wrapped into a coil having a very small diameter.

Although the present invention has been described in connection with certain exemplary embodiments, these embodiments are presented for instructional purposes and the present invention is not limited thereto. A number of constant current intervals other than five can comprise a period of the laser drive current signal. Intervals of varying current may also be included in the drive current signal. In some embodiments, the sample cell is not a substantially closed volume but rather is a substantially open volume of material to be analyzed through which a beam of laser radiation is passed before being detected. An evanescent wave of a beam of laser radiation passing through an optical fiber may, for example, be used to direct laser radiation through a material to be analyzed. Numerous on-airway structures for disposing a suitable length of optical fiber in human breath may be employed. Properties other than concentration can be detected and materials other than oxygen can be analyzed. The absorbance of liquids can be analyzed. Moreover, multiple combinations of selected ones of the structures and teachings disclosed herein for reducing the effects of unwanted reflections can be practiced. It is to be understood, therefore, that various changes, modifications, adaptations, and combinations of features of the above described embodiments may be practiced without departing from the spirit and scope of the invention as set forth in the appended claims.

We claim:

1. An absorption spectroscopy device, comprising:
   a laser diode emitting laser radiation;
   a quarter wave plate;
   a sample cell containing a volume of material to be analyzed; and
   a detector for measuring an absorption spectrum of said material to be analyzed, said laser radiation emitted from said laser diode passing through said quarter wave plate before passing through said sample cell and being incident on said detector.

2. An absorption spectroscopy device, comprising:
   a neutral density absorber;
   a sample cell;
   a detector; and
   a source of laser radiation emitting laser radiation, at least some of said laser radiation passing through said neutral density absorber and then through said sample cell before being incident on said detector.

3. The absorption spectroscopy device of claim 2, wherein said source of laser radiation comprises a laser diode.

4. The absorption spectroscopy device of claim 2, wherein said source of laser radiation comprises:
   a laser diode housing;
   a lens; and
   a volume of adhesive directly contacting said laser diode housing and said lens.

5. The absorption spectroscopy device of claim 2, wherein said source of laser radiation comprises a laser diode housing, said absorption spectroscopy device further comprising:
   a lens, said neutral density absorber being disposed between said lens and said laser diode housing.

6. The absorption device of claim 3, further comprising:
   means for determining a concentration of a material in said sample cell.

7. The absorption device of claim 6, further comprising:
   a thermoelectric cooler, said means for determining being coupled to said detector, to said laser diode and to said thermoelectric cooler.

8. The absorption device of claim 7, wherein said means for determining drives said laser diode with a drive current, said drive current having a stepped periodic waveform, each period of said stepped periodic waveform consisting essentially of only constant current intervals and brief current switching episodes.

9. The absorption device of claim 6, wherein said material is oxygen.

10. The absorption device of claim 8, wherein said material is oxygen.

11. A method, comprising the steps of:
    providing a neutral density absorber in a path of laser radiation between a source of laser radiation and a sample cell of an absorption spectroscopy device; and
    detecting laser radiation which passes through said neutral density absorber and then through said sample cell.

12. The method of claim 11, further comprising the step of:
    determining a concentration of a material in said sample cell.

* * * * *